US012686686B2

(12) United States Patent
Yin et al.

(10) Patent No.: US 12,686,686 B2
(45) Date of Patent: Jul. 21, 2026

(54) DAPHNANE DITERPENOID RESISTANT TO PROSTATE CANCER AND PREPARATION METHOD THEREOF

(71) Applicant: SUN YAT-SEN UNIVERSITY, Guangdong (CN)

(72) Inventors: Sheng Yin, Guangdong (CN); Xuelong Yan, Guangdong (CN); Junjian Wang, Guangdong (CN); Jialuo Huang, Guangdong (CN); Guihua Tang, Guangdong (CN)

(73) Assignee: SUN YAT-SEN UNIVERSITY, Guangzhou (CN)

( * ) Notice: Subject to any disclaimer, the term of this patent is extended or adjusted under 35 U.S.C. 154(b) by 806 days.

(21) Appl. No.: 18/157,529

(22) Filed: Jan. 20, 2023

(65) Prior Publication Data

US 2023/0159551 A1 May 25, 2023

Related U.S. Application Data

(63) Continuation-in-part of application No. PCT/CN2021/116955, filed on Sep. 7, 2021.

(30) Foreign Application Priority Data

Dec. 22, 2020 (CN) ......................... 202011524327.0

(51) Int. Cl.

| | |
|---|---|
| ***A61K 45/06*** | (2006.01) |
| ***A61P 35/00*** | (2006.01) |
| ***C07D 303/32*** | (2006.01) |
| ***C07D 491/18*** | (2006.01) |
| ***C07D 491/22*** | (2006.01) |

(52) U.S. Cl.

CPC ............ *C07D 491/22* (2013.01); *A61K 45/06* (2013.01); *A61P 35/00* (2018.01); *C07D 303/32* (2013.01); *C07D 491/18* (2013.01)

(58) Field of Classification Search

CPC ........ C07D 491/22; A61P 35/00; A61K 45/06

See application file for complete search history.

(56) References Cited

U.S. PATENT DOCUMENTS

2019/0352418 A1* 11/2019 Wilson ................... C07K 14/71

FOREIGN PATENT DOCUMENTS

| | | | | | |
|---|---|---|---|---|---|
| CN | 101531644 | A | | 9/2009 | |
| CN | 102344455 | A | | 2/2012 | |
| CN | 108689851 | A | | 10/2018 | |
| CN | 111410679 | A | | 7/2020 | |
| CN | 112538088 | A | | 3/2021 | |
| CN | 112920196 | A | * | 6/2021 | ................ A61P 3/06 |
| KR | 20140015798 | A | * | 2/2014 | ............ A61K 36/83 |
| WO | 2009096655 | A1 | | 8/2009 | |

OTHER PUBLICATIONS

CN 112920196 Machine translation (Year: 2021).*
KR 20140015798 Machine Translation (Year: 2014).*
Pan, Rongrong et al. "Daphnane Diterpenoids from Daphne genkwa Inhibit PI3K/Akt/mTOR Signaling and Induce Cell Cycle Arrest and Apoptosis in Human Colon Cancer Cells" Journal of Natural Products, vol. 83, Mar. 30, 2020 (Mar. 30, 2020), 1238-1248.
Nakasone, R. et al. "Promoting effects on hepatocyte growth factor production of daphnane diterpenoids from Daphne odora" Heterocycles, vol. 87, No. 5, Dec. 31, 2013 (Dec. 31, 2013), 1087-1092.
Baxter, R. L. et al. "Antileukaemic Properties of 12-Hydroxydaphnetoxin Derivatives" Bioorgmic & Medicinal Chemistry Letters, vol. 4, No. 22, Dec. 31, 1994 (Dec. 31, 1994), 2649-2652.

(Continued)

*Primary Examiner* — Sarah Pihonak
*Assistant Examiner* — Mikhail O'Donnel Robinson
(74) *Attorney, Agent, or Firm* — D'Ambrosio & Menon, PLLC; Usha Menon

(57) ABSTRACT

The invention relates to a daphnane diterpenoid resistant to a prostate cancer and a preparation method thereof. A daphnane diterpenoid compound as represented by formula (I) or formula (II) significantly inhibits the proliferation of various prostate cancer cells; the activities of some such compounds at a cellular level and an animal level are higher than that of the existing clinical targeting drug enzalutamide; and the daphnane diterpenoid compounds have strong synergistic effects when used in combination with the enzalutamide and are expected to become candidate drugs for treatment or adjuvant treatment of a castration-resistant prostate cancer.

I

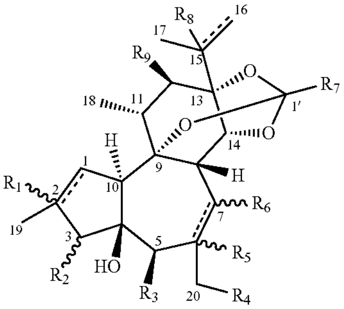

II

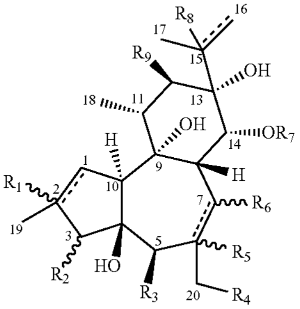

6 Claims, 5 Drawing Sheets

(56) References Cited

OTHER PUBLICATIONS

Brooks, G. et al. "Daphnane Diterpenes of Thymelaea Hirsuta" Phytochemistry, vol. 29, No. 7, Dec. 31, 1990 (Dec. 31, 1990), 2235-2237.
Wang, Chengrui et al. (Non-official translation: Study on Effective Constituents of the Root of Genkwa Flower II. Isolation and Structure of a New Antifertility Vinegar b of Lilodes Genkwa) Acta Chimica Sinica, vol. 39, No. 5, Oct. 31, 1981 (Oct. 31, 1981), 421-426.
Li, Feifei et al. "Daphnane-type diterpenes with inhibitory activities against human cancer cell lines from Daphne genkwa" Bioorganic & Medicinal Chemistry Letters, vol. 23, Mar. 15, 2013 (Mar. 15, 2013), 2500-2504.
Zhang, Shixuan et al. "Preparation of yuanhuacine and relative daphne diterpene esters from Daphne genkwa and structure-activity relationship of potent inhibitory activity against DNA topoisomerase I" Bioorganic & Medicinal Chemistry, vol. 14, Feb. 20, 2006 (Feb. 20, 2006), 3888-3895.
Huang, Shengzhuo et al. "Daphnane-type diterpene esters with cytotoxic and anti-HIV-1 activities from Daphne acutiloba Rehd" Phytochemistry, vol. 75, Dec. 21, 2011 (Dec. 21, 2011), 99-107.
Office Action received from Chinese Application No. 202011524327.0 dated Dec. 22, 2020.
English translation of International Search Report in International Application No. PCT/CN2021/116955, dated Feb. 8, 2022.
English translation of Notification to Grant Patent Right for Invention in Chinese Application No. 202011524327.0.

* cited by examiner

DAPHNANE DITERPENOID RESISTANT TO PROSTATE CANCER AND PREPARATION METHOD THEREOF

CROSS-REFERENCE TO RELATED APPLICATIONS

The present application is a Continuation in Part Application of International Application PCT/CN2021/116955, filed Sep. 7, 2021, which claims the benefit of and priority to Chinese Patent Application No. 202011524327.0, filed Dec. 22, 2020, the entire disclosures of which are incorporated herein by reference.

TECHNICAL FIELD

The present disclosure relates to a natural compound, a preparation method and use thereof, and in particular to a daphnane diterpenoid compound, a preparation method and use thereof in preparing a medicament resistant to castration-resistant prostate cancer.

BACKGROUND

Prostate cancer is a highly prevalent malignancy in middle-aged and elderly people. According to the latest cancer statistics from the American Cancer Society (ACS) in 2020, the incidence rate of the prostate cancer in the United States ranks highest and the mortality rate takes second among malignant tumors. In China, the incidence rate of prostate cancer is also soaring year by year with the changes in the standard of living and the pace of life.

In the later stage, the prostate cancer evolves into castration-resistant prostate cancer which is ineffective hormone therapy, resulting in metastasis, which is an important factor leading to patient death. The castration-resistant prostate cancer is closely related to the abnormally activated androgen receptor (AR) signaling pathway. The anti-androgen drugs enzalutamide and abiraterone, which were marketed in 2010 and 2011 respectively, can significantly improve patient survival. However, due to drug resistance, little effectiveness of treatment was achieved in the later stage. Therefore, the development of a new drug for the castration-resistant prostate cancer has important research significance and application value.

Natural products, due to their structural diversity and good bio-compatibility, are an important source for the research and development of the new drug. Literature research has shown that daphnane diterpenoids with a novel structure are abundant in Daphne plants. The daphnane diterpenoids are complex molecular structures with a 5/7/6 tricyclic carbon skeleton, and comprises multiple chiral centers that usually contain chiral hydroxyl groups at the positions of C3, C4, C5, C9, C13, C14, C20, etc., among which many compounds form a specific orthoester structure among the chiral hydroxyl groups at the C9, C13, and C14 positions.

Technical Problem

The daphnane diterpenoids have anti-HIV, anti-leukemia, anti-tumor, neuroprotective, insecticidal and cytotoxic activities, etc. Also, a research has found that such diterpenoids have a very significant inhibitory activity on prostate cancer cells, which is stronger than the existing clinical targeting drug enzalutamide at a cellular level and an animal level. However, the research on in-depth pharmacodynamics, structure-activity relationship and action mechanism of such diterpenoids in resisting to the prostate cancer is still lacking.

SUMMARY

According to the first aspect of the present disclosure, there is provided:

use of a daphnane diterpenoid compound in preparing a medicament for treatment or combination treatment of a castration-resistant prostate cancer, wherein the daphnane diterpenoid compound has a general formal as represented by formula I or formula II:

I

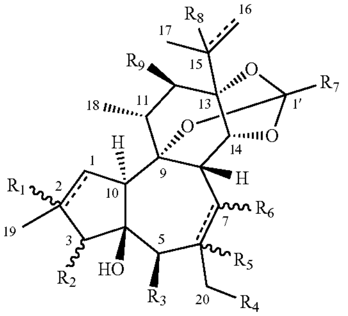

II

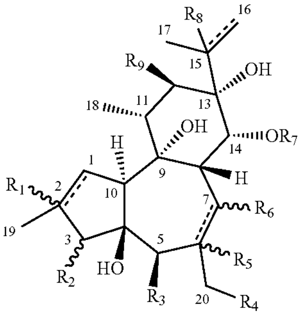

in the formula I and the formula II, a bond between C-1 and C-2 is a single bond or is a double bond, a bond between C-6 and C-7 is a single bond or is a double bond, and a bond between C-15 and C-16 is a single bond or is a double bond;

$R_1$ is selected from hydrogen or hydroxyl or $R_1$ is absent when a double bond is formed between C-1 and C-2;

$R_2$ is selected from hydrogen, hydroxyl, carbonyl, benzoyl or acetyl;

$R_3$ is selected from hydrogen, hydroxyl, acetyl, isovaleryl, crotonyl or benzoyl;

$R_4$ is selected from hydrogen, hydroxyl, acetyl, isobutyryl, 2-thienylcarbonyl, benzoyl or palmitoyl;

$R_5$ is selected from hydroxyl, fluorine, chlorine, bromine, and iodine, and forms a ternary epoxy with $R_6$ or $R_6$ is absent when a double bond is formed between C-6 and C-7;

$R_6$ is selected from hydrogen, hydroxyl, fluorine, chlorine, bromine and iodine, and forms a ternary epoxy with $R_5$ or $R_5$ is absent when a double bond is formed between C-6 and C-7;

in the formula I: $R_7$ is selected from methyl, phenyl, nonanyl, (1E, 3E)-nonadienyl, (1E, 3Z)-nonadienyl or (1E, 3E, 5E)-nonatrienyl;

in the formula II: $R_7$ is selected from hydrogen, benzoyl, acetyl, decanoyl, (2E, 4E)-decadienoyl, (2E, 4Z)-decadienoyl or (2E, 4E, 6E)-decatrienoyl;

$R_8$ is selected from hydrogen or hydroxyl or $R_8$ is absent when a double bond is formed between C-15 and C-16; and $R_9$ is selected from hydrogen, hydroxyl, acetyl, benzoyl, isobutyryl, butyryl or propionyl.

In some embodiments, the daphnane diterpenoid compound is selected from:

a compound of formula (III):

(III)

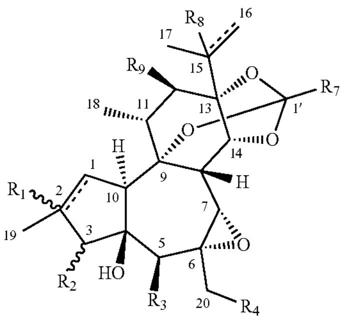

wherein the compound of formula (III) is selected from the group consisting of:

| Compound | $R_1$ | $R_2$ | $R_3$ | $R_4$ | $R_7$ | $R_8$ | $R_9$ |
|---|---|---|---|---|---|---|---|
| YH-1 | Δ1 | =O | OH | OH | Ph | Δ16 | OBu |
| YH-2 | Δ1 | =O | OH | OH | Ph | Δ16 | OiBu |
| YH-3 | Δ1 | =O | OH | OH | Ph | Δ16 | OProp |
| YH-4 | Δ1 | =O | OH | OH | Ph | Δ16 | OH |
| YH-5 | Δ1 | =O | OH | OG | Ph | Δ16 | OAc |
| YH-6 | Δ1 | =O | OH | OH | Ph | Δ16 | OAc |
| YH-7 | Δ1 | =O | OAc | OAc | Ph | Δ16 | OAc |
| YH-8 | Δ1 | =O | OH | OAc | Ph | Δ16 | OAc |
| YH-9 | Δ1 | =O | OH | OBz | Ph | Δ16 | OAc |
| YH-10 | Δ1 | =O | OH | OS | Ph | Δ16 | OAc |
| YH-11 | Δ1 | =O | OH | OH | Ph | Δ16 | OBz |
| YH-12 | Δ1 | =O | OAc | OAc | Ph | Δ16 | OBz |
| YH-13 | Δ1 | =O | OH | OAc | Ph | Δ16 | OBz |
| YH-14 | Δ1 | =O | OH | OH | A | Δ16 | OH |
| YH-15 | Δ1 | =O | OH | OH | A | Δ16 | OBu |
| YH-16 | Δ1 | =O | OH | OH | A | Δ16 | OBz |
| YH-17 | Δ1 | =O | OH | OH | D | Δ16 | OBz |
| YH-18 | Δ1 | =O | OAc | OAc | A | Δ16 | OBz |
| YH-19 | Δ1 | =O | OH | OAc | A | Δ16 | OBz |
| YH-20 | Δ1 | =O | OH | OBz | A | Δ16 | OBz |
| YH-21 | Δ1 | =O | OH | OS | A | Δ16 | OAc |
| YH-22 | Δ1 | =O | OH | OH | A | Δ16 | OAc |
| YH-23 | Δ1 | =O | OAc | OAc | A | Δ16 | OAc |
| YH-24 | Δ1 | =O | OH | OAc | A | Δ16 | OAc |
| YH-25 | Δ1 | =O | OH | OBz | A | Δ16 | OAc |
| YH-26 | Δ1 | =O | OH | OS | A | Δ16 | OAc |
| YH-27 | Δ1 | =O | OH | OG | A | Δ16 | OAc |
| YH-28 | Δ1 | =O | OH | OG | D | Δ16 | OBz |
| YH-29 | Δ1 | =O | OH | OH | B | Δ16 | OBz |
| YH-30 | Δ1 | =O | OH | OH | Me | Δ16 | OAc |
| YH-31 | Δ1 | =O | OH | OH | B | Δ16 | OAc |
| YH-32 | Δ1 | =O | OH | OH | D | Δ16 | OAc |
| YH-33 | Δ1 | =O | OH | OH | F | Δ16 | OAc |
| YH-34 | Δ1 | =O | OH | OH | F | Δ16 | OBz |
| YH-35 | αH | =O | OH | OH | Ph | Δ16 | OAc |
| YH-36 | αH | =O | OH | OH | Ph | Δ16 | OBz |
| YH-37 | Δ1 | =O | OH | OH | Da | H | OAc |
| YH-38 | αH | =O | OH | OH | Da | H | OAc |
| YH-39 | αH | =O | OH | OH | Ph | H | OBz |
| YH-40 | Δ1 | =O | OH | OH | Ph | H | OBz |
| YH-41 | Δ1 | =O | OH | OH | Ph | Δ16 | H |

-continued

| Compound | $R_1$ | $R_2$ | $R_3$ | $R_4$ | $R_7$ | $R_8$ | $R_9$ |
|---|---|---|---|---|---|---|---|
| YH-42 | αH | βO(CO)E | OH | OH | Ph | Δ16 | H |
| YH-43 | αH | βOH | OH | βOE | Ph | Δ16 | H; |

a compound of formula (IV):

(IV)

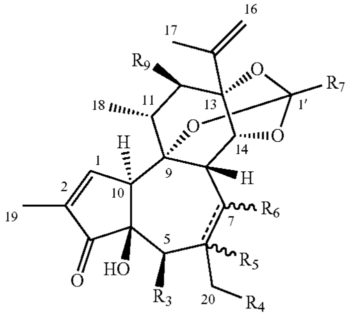

wherein the compound of formula (IV) is selected from the group consisting of:

| Compound | $R_3$ | $R_4$ | $R_5$ | $R_6$ | $R_7$ | $R_9$ |
|---|---|---|---|---|---|---|
| YH-44 | H | OH | Δ6 | H | Me | OBz |
| YH-45 | OH | OBz | βCl | αOH | Ph | OAc |
| YH-46 | OH | OBz | αOH | βCl | Ph | OAc |
| YH-47 | OH | OH | βCl | αOH | Ph | OAc |
| YH-48 | OH | OH | αOH | βCl | Ph | OAc |
| YH-49 | OH | OH | βCl | αOH | Ph | OBz |
| YH-50 | OH | OH | αOH | βCl | Ph | OBz |
| YH-51 | OH | OH | αOH | αOH | Ph | OBz |
| YH-52 | OH | OH | βBr | αOH | Ph | OBz |
| YH-53 | OH | OH | αOH | βBr | Ph | OBz; |

a compound of formula (V):

(V)

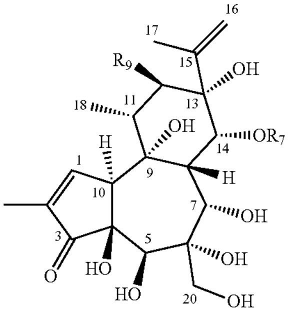

wherein the compound of formula (V) is selected from the group consisting of:

| Compound | $R_7$ | $R_9$ |
|---|---|---|
| YH-54 | COA | OAc |
| YH-55 | COA | OBz |
| YH-56 | Bz | OBz; |

and a compound of formula (VI):

(VI)

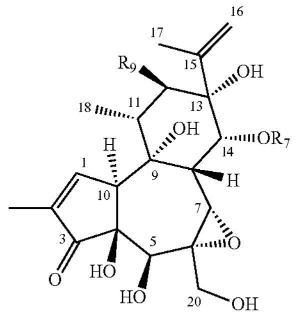

wherein the compound of formula (VI) is selected from the group consisting of:

| Compound | $R_7$ | $R_9$ |
|---|---|---|
| YH-57 | H | OBz |
| YH-58 | H | OAc |
| YH-59 | COD | OAc |
| YH-60 | Bz | OBz |
| YH-61 | COA | OH |
| YH-62 | COA | OAc |
| YH-63 | COA | OBz |
| YH-64 | COA | H; |

and wherein in formula (III), formula (IV), formula (V), and formula (VI):

A =

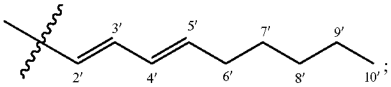

B =

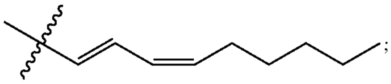

D =

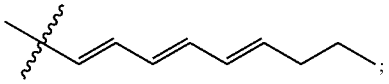

Da =

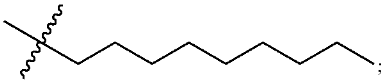

Bz =

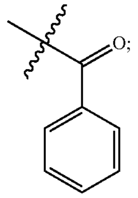

S =

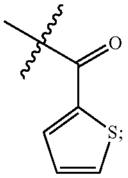

Bu =

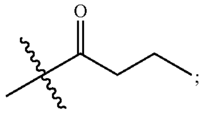

G =

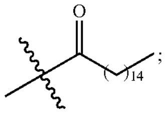

-continued iBu =

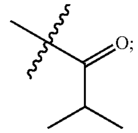

Prop =

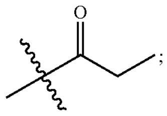

E =

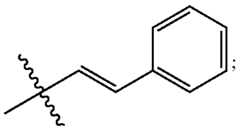

F =

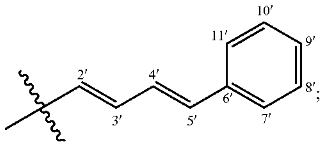

OAc =

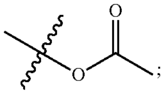

Me =

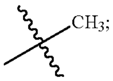

Ph =

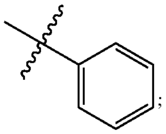

COA =

COD =

O(CO)E =

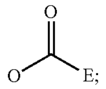

Δ1 is when $R_1$ is absent and a double bond is formed between C-1 and C-2;

Δ6 is when $R_5$ is absent and a double bond is formed between C-6 and C-7;

Δ16 is when $R_8$ is absent and a double bond is formed between C-15 and C-16;

α is when the identified substituent is on the opposite face of the hydroxyl group of the contiguous ring; and β is when the identified substituent is on the same face as the hydroxyl group of the contiguous ring.

In some embodiments, the daphnane diterpenoid compound is at least one selected from the group consisting of YH-6, YH-11, YH-16, YH-17, YH-22, YH-35, YH-36, YH-47, YH-48, YH-49, YH-50, YH-52 and YH-53.

In some embodiments, the daphnane diterpenoid compound further comprises a pharmaceutically acceptable derivative thereof.

In some embodiments, the pharmaceutically acceptable derivative is a salt thereof.

According to the second aspect of the present disclosure, there is provided:

a daphnane diterpenoid compound and a medicinal derivative thereof, the daphnane diterpenoid compound is as defined in the first aspect of the present disclosure.

In some embodiments, the daphnane diterpenoid compound is selected from the compounds of YH-8, YH-9, YH-10, YH-19, YH-20, YH-21, YH-24, YH-25, YH-26, YH-30, YH-33, YH-34, YH-37, YH-38, YH-39, YH-45, YH-46, YH-47, YH-48, YH-49, YH-50, YH-52, YH-53, YH-56, YH-57, YH-60 and YH-61.

According to the third aspect of the present disclosure, there is provided:

a composition for treatment or adjuvant treatment of a castration-resistant prostate cancer, an active ingredient of the composition comprises at least one of the daphnane diterpenoid compound defined in the first aspect of the present disclosure and the acceptably medicinal derivative thereof. In some embodiments, the pharmaceutically acceptable derivative is a salt thereof.

In some embodiments, the daphnane diterpenoid compound is selected from the compounds of YH-6, YH-11, YH-16, YH-17, YH-22, YH-35, YH-36, YH-8, YH-9, YH-10, YH-19, YH-20, YH-21, YH-24, YH-25, YH-26, YH-30, YH-33, YH-34, YH-37, YH-38, YH-39, YH-45, YH-46, YH-47, YH-48, YH-49, YH-50, YH-52, YH-53, YH-56, YH-57, YH-60 and YH-61, and an acceptably medicinal derivative thereof.

In some embodiments, the composition further comprises at least one compound having a therapeutic effect on the prostate cancer, preferably, the compound having the therapeutic effect on the prostate cancer is at least one selected from the group consisting of enzalutamide, abiraterone, cyclophosphamide, adriamycin, docetaxel and mitoxantrone.

According to the forth aspect of the present disclosure, there is provided:

a method for treatment or adjuvant treatment of a castration-resistant prostate cancer, comprising:

detecting to confirm that a patient suffers from the castration-resistant prostate cancer; and administering to the patient a therapeutic amount of a daphnane diterpenoid compound or a pharmaceutically acceptable salt, solvate, co-crystal thereof, wherein the daphnane diterpenoid compound is as defined in the first aspect of the present disclosure.

In some embodiments, the method further comprises administering to a patient at least one compound having a therapeutic effect on the prostate cancer, preferably, the compound having the therapeutic effect on the prostate cancer is at least one selected from the group consisting of enzalutamide, abiraterone, cyclophosphamide, adriamycin, docetaxel and mitoxantrone.

The present disclosure has the beneficial effects that: in the present disclosure, a daphnane diterpenoid compound is isolated or synthesised for the first time. Such compounds can significantly inhibit the proliferation of various prostate cancer cells; and in particular, Compound YH-52 has a higher activity at a cellular level and an animal level than that of the existing clinical targeting drug enzalutamide. In addition, the combination of the daphnane diterpenoid compound with enzalutamide can obtain a strong synergistic effect, therefore such compounds are expected to become candidate drugs for treatment of a castration-resistant prostate cancer.

DETAILED DESCRIPTION

Thirty-four (34) natural daphnane diterpenoids were isolated by the inventors from thymelaeaceae plants, daphne genkwa, and 30 derivatives were obtained from some compounds after being carried out with a structural modification. Relevant tests on the obtained series of diterpenoids for resisting to prostate cancer cells found a series of compounds that have a significant inhibitory activity on tumor cells and a stronger effect than that of the existing clinical targeting drug enzalutamide, among which one of the new compounds is expected to be a candidate drug for the treatment of the castration-resistant prostate cancer.

The technical scheme of the present disclosure will be explained in more detail with reference to the following embodiments. Unless otherwise specified, the reagents, equipment, and methods used in the present disclosure are those routinely commercially available and routinely used in the art.

In the present disclosure, research was carried out on thymelaeaceae plants (taking daphne genkwa as an example).

Equipment and reagents: a Bruker AM-400/500 spectrometer was used for recording NMR spectrum, and a TMS was used as an internal standard. Column chromatography silica gel (300-400 mesh): Qingdao Haiyang Chemical Co., Ltd.; $GF_{254}$ silica gel thin-layer chromatography prefabricated plate: Qingdao Haiyang Chemical Co., Ltd.; MCI filler (CHP20P, 75-150 μm): Mitsubishi Chemical Industries Ltd.; Sephadex (Sephadex LH-20): GE Company in USA; ODS filler (12 nm, S-50 μm): YMC. Co., Ltd in Japan; and other solvents and reagents: analytical pure (AR), Baishi Chemical Industry Co., Ltd, Tianjin, China.

Preparation of Daphnane Diterpenoid Compound

Twenty kg of daphne genkwa was taken, and crushed into coarse powder. Three times the volume of 95% ethanol was added, soaked for 1 week, and recovered the ethanol under reduced pressure after suction filtration. The soaking and extraction steps were repeated more than three times, and finally 1500 g of the ethanol extract of daphne genkwa was obtained. The extract of daphne genkwa was dispersed with 1 L of water, and then extracted three times with ethyl acetate. The ethyl acetate extract liquor were combined and concentrated under reduced pressure to obtain 300 g of ethyl acetate extract.

Figure 1:
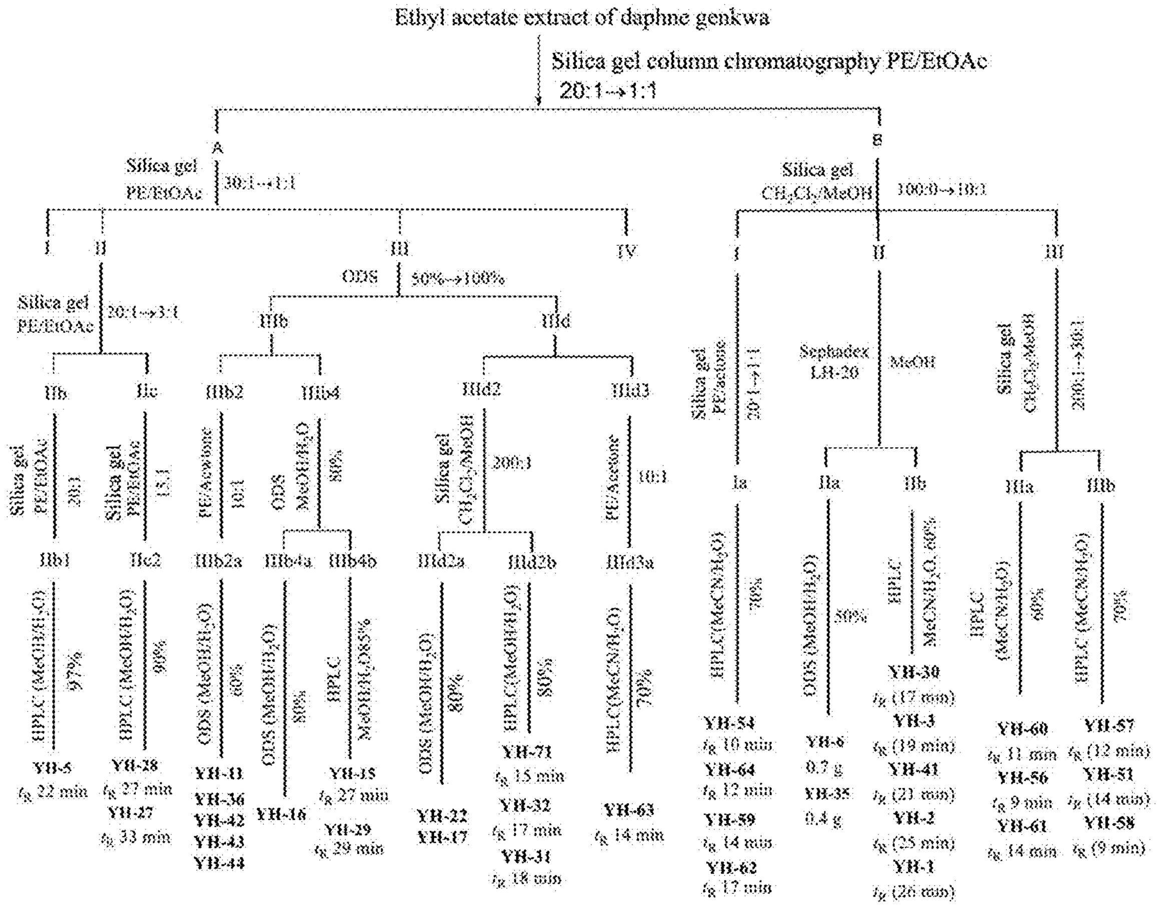
FIG. 1 is a flowchart showing the extraction and isolation of daphne genkwa.

The above ethyl acetate extract was taken and loaded on a silica gel column, initially segmented with the mixture of petroleum ether and ethyl acetate, the mixture of dichloromethane and methanol, then further isolated by ODS, MCI, Sephadex LH-20, finally purified by the semi-preparative high-performance liquid chromatography under the conditions of (acetonitrile:water) or (methanol:water), and 34 monomer compounds were obtained. FIG. 1 shows the specific isolation flowchart. The obtained partial daphnane diterpenoid compounds were structurally modified to prepare derivatives thereof Identification of Isolated Products

Example 1

Compound YH-30 was obtained by purifying with the semi-preparative HPLC. The structure and data of Compound YH-30 were as follows:

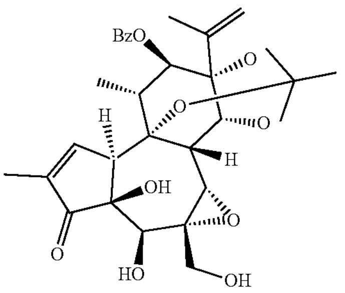

YH-30: $[\alpha]^{25}_{D}$+7.8 (c 0.230, $CH_2Cl_2$); UV (MeOH) Amax (log ε) 232 (4.21) nm; ECD (c $3.3\times10^{-4}$ M, MeCN) $\lambda_{max}$ (Δε) 252 (−2.44) nm; IR (KBr) $v_{max}$ 3445, 2925, 2856, 1705, 1632, 1451, 1401, 1379, 1301, 1268, 1108, 1070, 1026, 938, 913, 863 $cm^{-1}$; $^1$H NMR ($CDCl_3$, 400 MHz) $\delta_H$ 7.55 (1H, s, H-1), 4.20 (1H, s, H-5), 3.61 (1H, s, H-7), 3.59 (1H, d, J=2.4 Hz, H-8), 3.76 (1H, m, H-10), 2.52 (1H, q, J=7.2 Hz, H-11), 5.18 (1H, s, H-12), 4.84 (1H, d, J=2.4 Hz, H-14), 4.99 (2H, s, H-16), 1.84 (3H, s, $H_3$-17), 1.37 (3H, d, J=7.2 Hz, $H_3$-18), 1.76 (3H, br s, $H_3$-19), 3.81 (1H, d, J=12.0 Hz, H-20a), 3.90 (1H, d, J=12.0 Hz, H-20b), 1'-Me: 1.70 (3H, s); 12-OBz: 7.87 (2H, m), 7.44 (2H, m), 7.57 (1H, m); $^{13}$C NMR ($CDCl_3$, 100 MHz) $\delta_C$ 160.3 (C-1), 136.9 (C-2), 209.4 (C-3), 72.2 (C-4), 71.8 (C-5), 60.7 (C-6), 64.1 (C-7), 35.5 (C-8), 77.8 (C-9), 47.4 (C-10), 44.0 (C-11), 78.9 (C-12), 83.9 (C-13), 80.5 (C-14), 143.0 (C-15), 113.5 (C-16), 18.6 (C-17), 18.3 (C-18), 9.8 (C-19), 64.8 (C-20), 118.9 (C-1'), 1'-Me: 21.5, 12-OBz: 165.4, 129.7, 129.4×2, 128.6×2, 133.3; HRESIMS m/z 541.2070 $[M+H]^+$ (calcd for $C_{29}H_{33}O_{10}^+$, 541.2068).

Example 2

Compound YH-60 was obtained by isolating and purifying with the semi-preparative HPLC. The structure and data of Compound YH-60 were as follows:

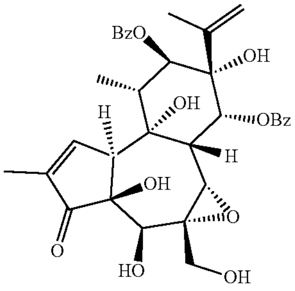

YH-60: $[\alpha]^{25}_{D}$-14.2 (c 0.148, $CH_2Cl_2$); UV (MeOH) $\lambda_{max}$ (log ε) 232 (4.50) nm; IR (KBr) $v_{max}$ 3418, 2925, 2855, 1704, 1631, 1452, 1379, 1315, 1270, 1178, 1108, 1070, 1026, 1010, 940, 915 $cm^{-1}$; $^1$H NMR ($CDCl_3$, 400 MHz) $\delta_H$ 7.63 (1H, s, H-1), 4.13 (1H, s, H-5), 3.36 (1H, s, H-7), 4.22 (1H, d, J=5.2 Hz, H-8), 3.51 (1H, s, H-10), 2.51 (1H, m, H-11), 5.22 (1H, d, J=2.2 Hz, H-12), 6.19 (1H, d, J=5.2 Hz, H-14), 5.04 (1H, s, H-16a), 5.34 (1H, s, H-16b), 1.88 (3H, s, $H_3$-17), 1.40 (3H, d, J=7.3 Hz, $H_3$-18), 1.75 (3H, br s, $H_3$-19), 3.34 (1H, d, J=12.3 Hz, H-20a), 4.00 (1H, d, J=12.3 Hz, H-20b), 12-OBz: 7.97 (2H, d, J=7.4 Hz), 7.49 (2H, m), 7.60 (1H, m); 14-OBz: 8.07 (2H, d, J=7.0 Hz), 7.28 (2H, m), 7.60 (1H, m); $^{13}$C NMR ($CDCl_3$, 100 MHz) $\delta_C$ 159.6 (C-1), 137.0 (C-2), 208.6 (C-3), 72.4 (C-4), 69.5 (C-5), 63.1 (C-6), 62.8 (C-7), 40.3 (C-8), 75.8 (C-9), 51.0 (C-10), 42.9 (C-11), 79.9 (C-12), 75.2 (C-13), 73.7 (C-14), 144.5 (C-15), 114.9 (C-16), 19.6 (C-17), 16.2 (C-18), 9.9 (C-19), 65.5 (C-20), 12-OBz: 165.8, 129.4, 129.6×2, 128.6×2, 133.3, 14-OBz: 166.6, 129.8, 130.0×2, 128.4×2, 133.4; HRESIMS m/z 619.2168 $[M-H]^-$ (calcd for $C_{34}H_{35}O_{11}^-$, 619.2185).

Preparation of Derivatives

The raw material compounds used in the following examples were YH-6, YH-11, YH-16 and YH-22. The structures of these compounds were as follows:

YH-6

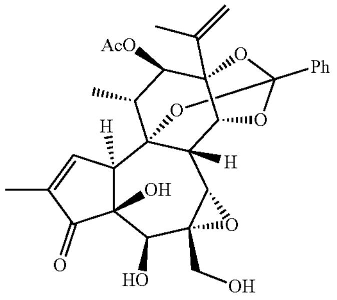

YH-11

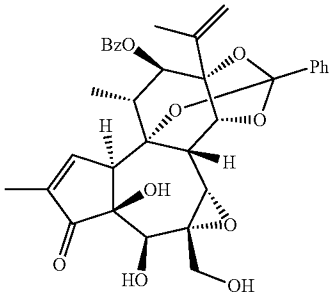

YH-16

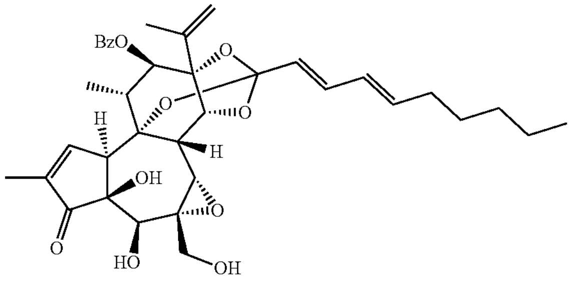

YH-22

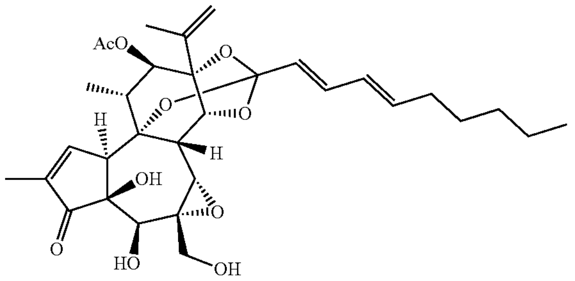

Example 3: Preparation of YH-7 and YH-8

Compound YH-6 (30 mg) was taken and dissolved in 2 mL of pyridine, and then stirred under the protection of $N_2$.

One-hundred (100) μL of acetic anhydride was pumped into with an injector and heated for reaction at 50° C. Two products were found in thin layer detection. When the raw material was basically reacted, 3 mL of water was added to stop the reaction, and then EtOAc (5 mL) was used to extract three times. After the reaction product was purified with a preparative thin layer ($CH_2Cl_2$/MeOH, 50:1), YH-7 (10 mg) and YH-8 (15 mg) were obtained. The structure and data were as follows:

YH-7

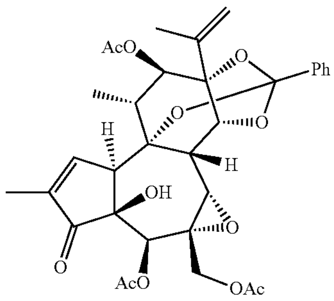

YH-8

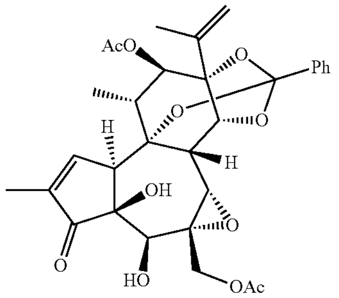

YH-7: UV (MeOH) $\lambda_{max}$ (log) 240 (3.70) nm; $^1$HNMR (400 MHz, $CDCl_3$) $\delta_H$ 7.72 (2H, m), 7.49 (1H, br s), 7.39 (3H, m), 5.57 (1H, s), 5.05 (2H, s, overlap), 5.02 (1H, s), 4.91 (1H, d, J=2.5 Hz), 4.80 (1H, d, J=12.0 Hz), 4.06 (1H, m), 3.67 (1H, d, J=2.5 Hz), 3.63 (1H, d, J=12.0 Hz), 3.53 (1H, s), 3.07 (1H, s), 2.37 (1H, q, J=7.3 Hz), 2.20 (3H, s), 2.03 (6H, s), 1.88 (3H, s), 1.75 (1H, br s), 1.31 (3H, d, J=7.3 Hz); $^{13}$C NMR (100 MHz, $CDCl_3$) $\delta_C$ 10.0, 18.1, 18.8, 20.6, 20.7, 21.1, 35.4, 43.9, 47.9, 59.5, 64.2, 66.3, 68.4, 71.8, 78.1, 78.3, 80.5, 84.1, 113.5, 117.9, 126.0, 128.0, 129.7, 135.1, 137.1, 143.0, 158.2, 168.8, 169.6, 170.6, 205.6; MS m/z 625.2 $[M+H]^+$ 659.2 $[M+Cl]^-$.

YH-8: $[\alpha]_D^{25}$+12.0 (c 0.47, MeOH), UV (MeOH) $\lambda_{max}$ (log) 241 (4.16) nm; IR (KBr) $v_{max}$ 3469, 2929, 1738, 1698, 1234, 1082, and 1024 $cm^{-1}$; $^1$H NMR ($CDCl_3$, 400 MHz) $\delta_H$ 7.57 (1H, br s, H-1), 4.30 (1H, s, H-5), 3.51 (1H, s, H-7), 3.61 (1H, d, J=2.6 Hz, H-8), 3.96 (1H, m, H-10), 2.46 (1H, q, J=7.3 Hz, H-11), 5.07 (1H, s, H-12), 4.88 (1H, d, J=2.6 Hz, H-14), 5.04 (1H, s, H-16a), 5.02 (1H, s, H-16b), 1.88 (3H, s, $H_3$-17), 1.35 (3H, d, J=7.3 Hz, $H_3$-18), 1.78 (3H, brs, $H_3$-19), 4.83 (1H, d, J=12.0 Hz, H-20a), 3.92 (1H, d, J=12.0 Hz, H-20b). 1'-Ph: 7.71 (2H, m), 7.38 (2H, m), 7.38 (1H, m), 12-OAc: 2.02 (3H. s). 20-OAc: 2.09 (3H, s); $^{13}$C NMR ($CDCl_3$, 100 MHz) $\delta_C$ 160.1 (C-1), 136.9 (C-2), 209.2 (C-3), 72.2 (C-4), 69.8 (C-5), 59.4 (C-6), 64.0 (C-7), 35.3 (C-8), 78.6 (C-9), 47.3 (C-10), 44.0 (C-11), 78.2 (C-12), 84.0 (C-13), 80.7 (C-14), 143.0 (C-15), 113.5 (C-16), 18.8 (C-17), 18.3 (C-18), 9.9 (C-19), 65.7 (C-20), 117.9 (C-1'). 1'-Ph: 135.2, 126.0×2, 128.0×2, 129.6. 12-OAc: 169.6, 21.1. 20-OAc: 170.6, 20.8; HRESIMS m/z 583.2179 $[M+H]^+$ (calcd for $C_{31}H_{35}O_{11}^+$, 583.2174).

Example 4: Preparation of Compound YH-9

Compound YH-6 (20 mg) was taken and dissolved in 2 mL of dichloromethane. One-hundred (100) L of triethylamine ($Et_3N$) was added under stirring, and 100 L of benzoyl chloride was added for reaction for 30 min. When the raw material was reacted, 5 mL of $H_2O$ was added to stop the reaction, and then dichloromethane (3×5 mL) was used to extract. The organic phase was concentrated, then purified with a gel (Sephadex LH-20, MeOH) and a preparative thin layer ($CH_2Cl_2$/MeOH, 50:1), and finally Compound YH-9 (11 mg) was obtained. The structure and data of the compound were as follows:

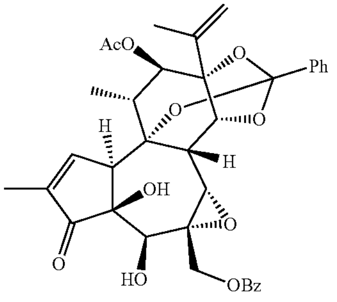

YH-9: $[\alpha]_D^{25}$+24 (c 0.43, MeOH); UV (MeOH) $\lambda_{max}$ (log) 231 (3.50) nm; IR (KBr) $v_{max}$ 3465, 2925, 1721, 1274, 1240, 1082, and 1023 $cm^{-1}$; $^1$H NMR ($CDCl_3$, 400 MHz) $\delta_H$ 7.58 (1H, br s, H-1), 4.39 (1H, s, H-5), 3.59 (1H, s, H-7), 3.66 (1H, d, J=2.3 Hz, H-8), 4.01 (1H, br s, H-10), 2.49 (1H, q, J=7.3 Hz, H-11), 5.08 (1H, s, H-12), 4.90 (1H, d, J=2.3 Hz, H-14), 5.03 (1H, s, H-16a), 5.05 (1H, s, H-16b), 1.88 (3H, s, $H_3$-17), 1.37 (3H, d, J=7.3 Hz, $H_3$-18), 1.79 (3H, br s, $H_3$-19), 5.13 (1H, d, J=11.9 Hz, H-20a), 4.10 (1H, d, J=11.9 Hz, H-20b). 1'-Ph: 7.71 (2H, m), 7.38 (2H, m), 7.38 (1H, m). 12-OAc: 2.02 (3H. s). 20-OBz: 8.05 (2H, d, J=7.7 Hz), 7.43 (2H, t, J=7.7 Hz), 7.56 (1H, m); $^{13}$C NMR ($CDCl_3$, 100 MHz) $\delta_C$ 160.1 (C-1), 136.9 (C-2), 209.2 (C-3), 72.3 (C-4), 69.8 (C-5), 59.7 (C-6), 64.2 (C-7), 35.3 (C-8), 78.6 (C-9), 47.3 (C-10), 44.0 (C-11), 78.3 (C-12), 84.1 (C-13), 80.7 (C-14), 143.0 (C-15), 113.5 (C-16), 18.8 (C-17), 18.3 (C-18), 9.9 (C-19), 66.6 (C-20), 117.9 (C-1'). 1'-Ph: 135.2, 126.0×2, 128.0×2, 129.6. 12-OAc: 169.6, 21.1. 20-OBz: 166.2, 129.8, 129.7×2, 128.4×2, 133.2; ESIMS m/z 645.2 $[M+H]^+$, 679.2 $[M+Cl]^-$; HRESIMS m/z 643.2184 $[M-H]^-$ (calcd for $C_{36}H_{35}O_{11}^-$, 643.2185).

Example 5: Preparation of Compound YH-10

Compound YH-6 (20 mg) was taken and dissolved in anhydrous pyridine. Nitrogen was then added for protection after vacuuming, and 100 μL of 2-thiophenecarbonyl chloride was pumped into with an injector and heated for reaction at 50° C. for 2 h. After the completion of the reaction, 5 mL of water was added to quench, and then EtOAc (3×5 mL) was used to extract. The organic phase was concentrated, then purified with a preparative thin layer ($CH_2Cl_2$/MeOH, 50:1) and a gel (Sephadex LH-20, MeOH), and finally Compound YH-10 (12 mg) was obtained. The structure and data of the compound were as follows:

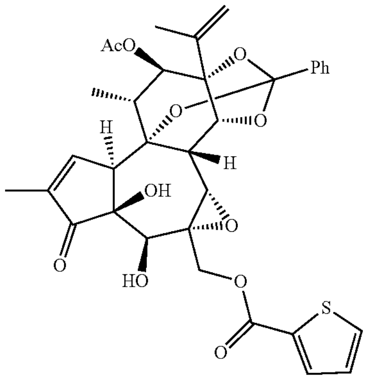

YH-10: Colorless oil: $[\alpha]_D^{25}$+17.1 (c 0.23, MeOH); UV (MeOH) $\lambda_{max}$ (log) 245 (3.94) nm; IR (KBr) $\nu_{max}$ 3476, 2924, 1706, 1257, 1230, 1081, and 750 $cm^{-1}$; $^1H$ NMR ($CDCl_3$, 400 MHz) $\delta_H$ 7.57 (1H, br s, H-1), 4.36 (1H, s, H-5), 3.57 (1H, s, H-7), 3.64 (1H, d, J=2.5 Hz, H-8), 3.98 (1H, m, H-10), 2.48 (1H, q, J=7.2 Hz, H-11), 5.07 (1H, s, H-12), 4.90 (1H, d, J=2.5 Hz, H-14), 5.05 (1H, s, H-16a), 5.02 (1H, s, H-16b), 1.88 (3H, s, $H_3$-17), 1.36 (3H, d, J=7.2 Hz, $H_3$-18), 1.79 (3H, br s, $H_3$-19), 5.12 (1H, d, J=11.9 Hz, H-20a), 4.05 (1H, d, J=11.9 Hz, H-20b). 1'-Ph: 7.71 (2H, m), 7.38 (2H, m), 7.38 (1H, m). 12-OAc: 2.02 (3H. s). 2-thenoyl: 7.82 (1H, dd, J=3.7, 1.1 Hz), 7.09 (1H, dd, J=4.8, 3.9 Hz), 7.55 (1H, dd, J=4.8, 1.1 Hz); $^{13}C$ NMR ($CDCl_3$, 100 MHz) $\delta_C$ 160.2 (C-1), 137.0 (C-2), 209.2 (C-3), 72.3 (C-4), 69.7 (C-5), 59.7 (C-6), 64.0 (C-7), 35.3 (C-8), 78.6 (C-9), 47.3 (C-10), 44.0 (C-11), 78.2 (C-12), 84.1 (C-13), 80.7 (C-14), 143.0 (C-15), 113.6 (C-16), 18.9 (C-17), 18.3 (C-18), 10.0 (C-19), 66.6 (C-20), 117.9 (C-1'). 1'-Ph: 135.2, 126.0×2, 128.1×2, 129.7. 12-OAc: 169.7, 21.2. 2-thenoyl: 161.8, 133.1, 133.9, 127.9, 132.8; ESIMS m/z 651.2 $[M+H]^+$ $[M+Cl]^-$; HRESIMS m/z 651.1858 (calcd for $C_{34}H_{35}O_{11}S^+$, 651.1855).

Example 6: Preparation of Compounds YH-12 and YH-13

Compound YH-11 (30 mg) was taken and dissolved in 2 mL of pyridine. Followed by stirring under the protection of $N_2$, 100 μL of acetic anhydride was pumped into with an injector and heated for reaction at 50° C. Two products were found in thin layer detection. When the raw material was basically reacted, 3 mL of water was added to stop the reaction, and EtOAc (5 mL) was used to extract three times. After the reaction products were purified with a preparative thin layer ($CH_2Cl_2$/MeOH, 50:1), YH-12 (13 mg) and YH-13 (10 mg) were obtained. The structure and data of the compounds were as follows:

YH-12

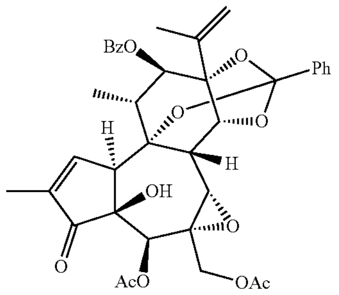

-continued

YH-13

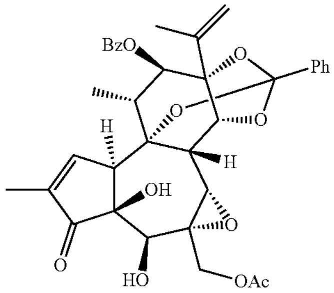

YH-12: $[\alpha]^{25}$+63.3 (c 0.33, MeOH); UV (MeOH) $\lambda_{max}$ (log) 231 (3.99) nm; IR (KBr) $\nu_{max}$ 3445, 2925, 1710, 1268, 1080, and 713 $cm^{-1}$; $^1H$ NMR ($CDCl_3$, 400 MHz) $\delta_H$ 7.50 (1H, br s, H-1), 5.55 (1H, s, H-5), 3.59 (1H, s, H-7), 3.78 (1H, d, J=2.5 Hz, H-8), 4.08 (1H, m, H-10), 2.55 (1H, q, J=7.2 Hz, H-11), 5.28 (1H, s, H-12), 5.05 (1H, d, J=2.5 Hz, H-14), 5.09 (1H, s, H-16a), 5.04 (1H, s, H-16b), 1.92 (3H, s, $H_3$-17), 1.40 (3H, d, J=7.2 Hz, $H_3$-18), 1.74 (3H, br s, $H_3$-19), 4.79 (1H, d, J=12.0 Hz, H-20a), 3.64 (1H, d, J=12.0 Hz, H-20b). 1'-Ph: 7.75 (2H, m), 7.40 (2H, m), 7.40 (1H, m). 12-OBz: 7.94 (2H, m), 7.48 (2H, m), 7.61 (1H, m). 5-OAc: 2.14 (3H, s). 20-OAc: 2.03 (3H, s); $^{13}C$ NMR ($CDCl_3$, 100 MHz) $\delta_C$ 158.0 (C-1), 137.2 (C-2), 205.4 (C-3), 71.7 (C-4), 68.4 (C-5), 59.6 (C-6), 64.2 (C-7), 35.9 (C-8), 78.4 (C-9), 47.9 (C-10), 44.0 (C-11), 78.9 (C-12), 84.3 (C-13), 80.6 (C-14), 142.9 (C-15), 113.8 (C-16), 18.9 (C-17), 18.2 (C-18), 10.0 (C-19), 66.4 (C-20), 118.0 (C-1'). 1'-Ph: 135.1, 126.0×2, 128.1×2, 129.7. 12-OBz: 165.4, 129.7, 129.5×2, 128.6×2, 133.4. 5-OAc: 168.8, 20.7. 20-OAc: 170.6, 20.3; ESIMS m/z 687.3 $[M+H]^+$; HRESIMS m/z 687.2420 $[M+H]^+$ (calcd for $C_{38}H_{39}O_{12}^+$, 687.2436).

YH-13: white powder; $[\alpha]^{25}$+50.2 (c 0.43, MeOH); UV (MeOH) $\lambda_{max}$ (log) 232 (4.02) nm; IR (KBr) $\nu_{max}$ 3446, 2925, 1908, 1451, 1365, 1267, 1241, 978, 713 $cm^{-1}$; $^1H$NMR ($CDCl_3$, 400 MHz) $\delta_H$ 7.59 (1H, br s, H-1), 4.28 (1H, d, J=2.4 Hz, H-5), 3.59 (1H, s, H-7), 3.73 (1H, d, J=2.5 Hz, H-8), 3.98 (1H, m, H-10), 2.64 (1H, q, J=7.3 Hz, H-11), 5.32 (1H, s, H-12), 5.01 (1H, d, J=2.5 Hz, H-14), 5.08 (1H, s, H-16a), 5.03 (1H, s, H-16b), 1.92 (3H, s, $H_3$-17), 1.45 (3H, d, J=7.3 Hz, $H_3$-18), 1.77 (3H, br s, $H_3$-19), 4.84 (1H, d, J=12.0 Hz, H-20a), 3.92 (1H, d, J=12.0 Hz, H-20b). 1'-Ph: 7.75 (2H, m), 7.40 (2H, m), 7.40 (1H, m). 12-OBz: 7.92 (2H, m), 7.47 (2H, m), 7.59 (1H, m). 20-OAc: 2.09 (3H, s); $^{13}C$ NMR ($CDCl_3$, 100 MHz) $\delta_C$ 160.1 (C-1), 136.9 (C-2), 209.2 (C-3), 72.1 (C-4), 69.8 (C-5), 59.4 (C-6), 64.1 (C-7), 35.7 (C-8), 78.6 (C-9), 47.3 (C-10), 44.1 (C-11), 78.9 (C-12), 84.2 (C-13), 80.7 (C-14), 142.9 (C-15), 113.8 (C-16), 18.9 (C-17), 18.4 (C-18), 9.9 (C-19), 65.8 (C-20), 118.0 (C-1'). 1'-Ph: 135.1, 126.0×2, 128.1×2, 129.7. 12-OBz: 165.4, 129.7, 129.5×2, 128.6×2, 133.4. 20-OAc: 170.6, 20.9; ESIMS m/z 645.3 $[M+H]^+$; HRESIMS m/z 645.2339 $[M+H]^+$ (calcd for $C_{36}H_{37}O_{11}^+$, 645.2330).

Example 7: Preparation of Compound YH-25

Compound YH-22 (23 mg) was taken, and the product was prepared with reference to the method in Example 4. After the obtained product was purified with a gel (Sephadex LH-20, MeOH) and a preparative thin layer ($CH_2Cl_2$/MeOH, 100:1), Compound YH-25 (15 mg) was obtained. The structure and data of the compound were as follows:

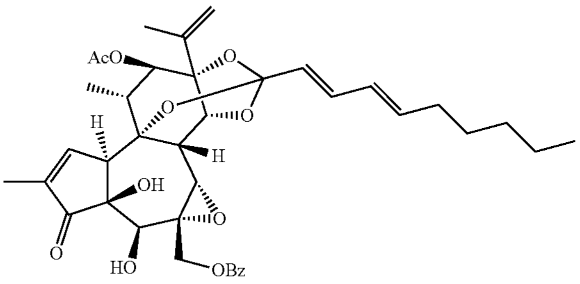

YH-25: Colorless oil; $[\alpha]_D^{25}$+28.5 (c 0.067, MeOH); UV (MeOH) $\lambda_{max}$ (log) 230 (4.50) nm; IR (KBr) $v_{max}$ 3459, 2926, 1719, 1273, 1230, 1026, and 711 $cm^{-1}$; $^1$HNMR ($CDCl_3$, 400 MHz) $\delta_H$ 7.57 (1H, m, H-1), 4.37 (1H, s, H-5), 3.52 (1H, s, H-7), 3.57 (1H, d, J=2.5 Hz, H-8), 3.91 (1H, m, H-10), 2.40 (1H, q, J=7.2 Hz, H-11), 4.99 (1H, s, H-12), 4.76 (1H, d, J=2.5 Hz, H-14), 5.01 (1H, s, H-16a), 4.97 (1H, s, H-16b), 1.84 (3H, s, $H_3$-17), 1.30 (3H, d, J=7.2 Hz, H-18), 1.78 (3H, br s, $H_3$-19), 5.12 (1H, d, J=11.9 Hz, H-20a), 4.07 (1H, d, J=11.9 Hz, H-20b), 5.64 (1H, d, J=15.5 Hz, H-2'), 6.66 (1H, dd, J=15.5, 10.6 Hz, H-3'), 6.03 (1H, dd, J=15.0, 10.6 Hz, H-4'), 5.85 (1H, dd, J=15.0, 7.4 Hz, H-5'), 2.08 (2H, m, $H_2$-6'), 1.37 (2H, m, $H_2$-7'), 1.26 (2H, m, $H_2$-8'), 1.26 (2H, m, $H_2$-9'), 0.87 (3H, t, J=6.9 Hz, H-10'). 12-OAc: 1.99 (3H. s). 20-OBz: 8.04 (2H, d, J=7.3 Hz), 7.44 (2H, m), 7.56 (1H, m); $^{13}$C NMR ($CDCl_3$, 100 MHz) $\delta_C$ 160.2 (C-1), 136.9 (C-2), 209.2 (C-3), 72.3 (C-4), 69.7 (C-5), 59.7 (C-6), 64.1 (C-7), 35.2 (C-8), 78.1 (C-9), 47.3 (C-10), 43.9 (C-11), 78.2 (C-12), 83.6 (C-13), 80.3 (C-14), 143.1 (C-15), 113.3 (C-16), 18.7 (C-17), 18.2 (C-18), 9.9 (C-19), 66.6 (C-20), 117.1 (C-1'), 122.2 (C-2'), 135.0 (C-3'), 128.5 (C-4'), 139.3 (C-5'), 32.6 (C-6'), 28.7 (C-7'), 31.3 (C-8'), 22.5 (C-9'), 14.0 (C-10'). 12-OAc: 169.7, 21.1. 20-OBz: 166.2, 129.7, 129.7×2, 128.4×2, 133.1; ESIMS m/z 691.3 $[M+H]^+$, 725.2 $[M+Cl]^-$; HRESIMS m/z 689.2962 $[M-H]^-$ (calcd for $C_{39}H_{45}O_{11}$, 689.2967).

Example 8: Preparation of Compound YH-33

Compound YH-22 (30 mg) was taken and dissolved in dichloromethane. Ten (10) mg of Grubbs second-generation catalyst was then added, and nitrogen was added for protection after vacuuming. Two hundred (200) μL of styrene was pumped into with an injector, and then heated for reaction under stirring at 40° C. for 1 h. The catalyst was removed by filtration, the filtrate was concentrated and then purified with an HPLC ($MeCN/H_2O$, 75%, 3 mL/min), and finally Compound YH-33 (15 mg, $t_R$=10 min) was obtained. The structure and data of the compound were as follows:

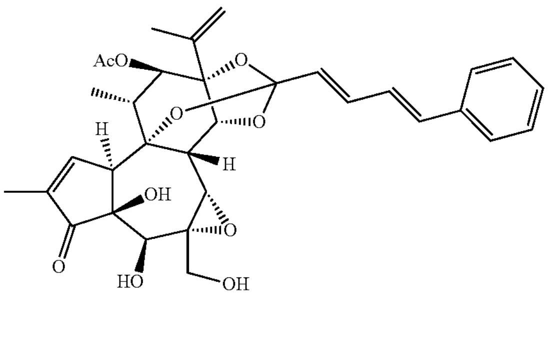

YH-33: $[\alpha]_D^{25}$+4.2 (c 0.33, MeOH); UV (MeOH) $\lambda_{max}$ (log) 286 (4.26) nm; $^1$H NMR ($CDCl_3$, 400 MHz) $\delta_H$ 7.59 (1H, br s, H-1), 4.27 (1H, s, H-5), 3.57 (1H, s, H-7), 3.53 (1H, d, J=2.5 Hz, H-8), 3.85 (1H, m, H-10), 2.39 (1H, q, J=7.3 Hz, H-11), 5.00 (1H, s, H-12), 4.79 (1H, d, J=2.5 Hz, H-14), 5.03 (1H, br s, H-16a), 4.97 (1H, br s, H-16b), 1.85 (3H, s, $H_3$-17), 1.31 (3H, d, J=7.3 Hz, $H_3$-18), 1.80 (3H, br s, $H_3$-19), 3.94 (1H, d, J=12.4 Hz, H-20a), 3.81 (1H, d, J=12.4 Hz, H-20b), 5.88 (1H, d, J=14.9 Hz, H-2'), 6.86 (1H, dd, J=14.9, 10.0 Hz, H-3'), 6.77 (1H, dd, J=15.1, 10.0 Hz, H-4'), 6.69 (1H, d, J=15.1 Hz, H-5'), 7.40 (2H, m, H-7'/H-11'), 7.32 (1H, dd, J=7.5, 7.5 Hz, H-8'/H-10'), 7.26 (1H, m, H-9'); 12-OAc: 2.00 (3H, s); $^{13}$C NMR ($CDCl_3$, 100 MHz) $\delta_C$ 160.3 (C-1), 136.9 (C-2), 209.4 (C-3), 72.2 (C-4), 71.9 (C-5), 60.5 (C-6), 64.2 (C-7), 35.4 (C-8), 78.3 (C-9), 47.4 (C-10), 44.0 (C-11), 78.2 (C-12), 83.8 (C-13), 80.5 (C-14), 143.0 (C-15), 113.4 (C-16), 18.7 (C-17), 18.3 (C-18), 9.9 (C-19), 65.1 (C-20), 116.8 (C-1'), 124.9 (C-2'), 134.8 (C-3'), 127.0 (C-4'), 136.0 (C-5'), 136.7 (C-6'), 126.7 (C-7'/C-11'), 128.6 (C-8'/10'), 128.1 (C-9'), 12-OAc: 169.7, 21.2; HRESIMS m/z 615.2206 $[M+Na]^+$ (calcd for, $C_{33}H_{36}O_{10}Na+$, 615.2201) and 627.1993 $[M+Cl]^-$ (calcd for $C_{33}H_{36}O_{10}Cl^-$, 627.2002).

Example 9: Preparation of Compound YH-34

Compound YH-16 (30 mg) was taken, and the product was prepared with reference to the method in Example 8. After the obtained product was purified with an HPLC ($MeCN/H_2O$, 80%, 3 mL/min), Compound YH-34 (16 mg, $t_R$=14 min) was obtained. The structure and data of the compound were as follows:

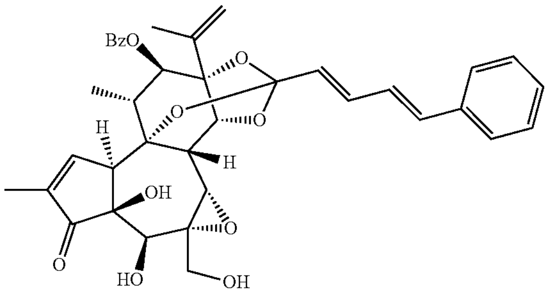

YH-34: $[\alpha]^{25}$+27.8 (c 0.13, MeOH); UV (MeOH) $\lambda_{max}$ (log) 285 (4.24) nm; $^1$H NMR ($CDCl_3$, 500 MHz) $\delta_H$ 7.61 (1H, br s, H-1), 4.23 (1H, s, H-5), 3.66 (1H, s, H-7), 3.65 (1H, d, J=2.7 Hz, H-8), 3.87 (1H, m, H-10), 2.58 (1H, q, J=7.2 Hz, H-11), 5.24 (1H, s, H-12), 4.93 (1H, d, J=2.7 Hz, H-14), 5.04 (1H, br s, H-16a), 5.02 (1H, br s, H-16b), 1.89 (3H, s, $H_3$-17), 1.41 (3H, d, J=7.2 Hz, $H_3$-18), 1.79 (3H, br s, $H_3$-19), 3.94 (1H, d, J=12.2 Hz, H-20a), 3.83 (1H, d, J=12.2 Hz, H-20b), 5.91 (1H, d, J=15.2 Hz, H-2'), 6.90 (1H, dd, J=15.2, 10.5 Hz, H-3'), 6.78 (1H, dd, J=15.4, 10.5 Hz, H-4'), 6.73 (1H, d, J=15.4 Hz, H-5'), 7.41 (2H, d, J=7.6 Hz, H-7'/H-11'), 7.33 (1H, dd, J=7.6, 7.6 Hz, H-8'/H-10'), 7.26 (1H, m, H-9'); 12-OBz: 7.90 (2H, d, J=7.6 Hz), 7.46 (2H, dd, J=7.6, 7.6 Hz), 7.58 (1H, dd, J=7.6, 7.6 Hz); $^{13}$C NMR ($CDCl_3$, 125 MHz) $\delta_C$ 160.2 (C-1), 137.0 (C-2), 209.3 (C-3), 72.2 (C-4), 71.8 (C-5), 60.6 (C-6), 64.0 (C-7), 35.8 (C-8), 78.4 (C-9), 47.4 (C-10), 44.1 (C-11), 78.9 (C-12), 84.0 (C-13), 80.5 (C-14), 142.9 (C-15), 113.7 (C-16), 18.8 (C-17), 18.3 (C-18), 9.9 (C-19), 64.7 (C-20), 116.9 (C-1'), 124.8 (C-2'), 134.8 (C-3'), 127.0 (C-4'), 136.1 (C-5'), 136.7

(C-6'), 126.7 (C-7'/C-11'), 128.6 (C-8'/10'), 128.1 (C-9'), 12-OBz: 129.6, 129.5×2, 128.7×2, 133.3; HRESIMS m/z 689.2147 $[M+Cl]^-$ (calcd for $C_{38}H_{38}O_{10}Cl^-$, 689.2159).

Example 10: Preparation of Compound YH-37

Compound YH-22 (20 mg) was taken and dissolved in 3 mL of methanol. Twenty (20) mg of palladium-carbon catalyst was then added, and hydrogen was added for protection after vacuuming. Followed by stirring for reaction at a room temperature for 30 min, the palladium-carbon was removed by filtration. The filtrate was concentrated, then purified directly with an HPLC ($MeCN/H_2O$, 95%, 3 mL/min), and finally Compound YH-37 (12 mg, $t_R$=14 min) was obtained. The structure and data of the compound were as follows:

YH-37

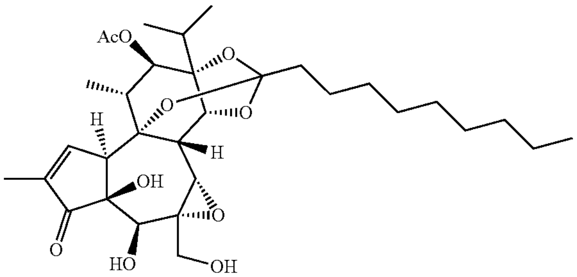

YH-37: $[\alpha]^{25}$+87.0 (c 0.033, MeOH); UV (MeOH) $\lambda_{max}$ (log) 243 (4.03) nm; IR (KBr) $v_{max}$ 3465, 2925, 1744, 1698, 1230, 1027, and 936 $cm^{-1}$; $^1H$ NMR ($CDCl_3$, 400 MHz) $\delta_H$ 7.53 (1H, br s, H-1), 4.23 (1H, s, H-5), 3.49 (1H, s, H-7), 3.34 (1H, d, J=2.4 Hz, H-8), 3.73 (1H, m, H-10), 2.30 (1H, q, J=7.3 Hz, H-11), 4.93 (1H, s, H-12), 4.44 (1H, d, J=2.4 Hz, H-14), 1.85 (1H, m, H-15), 0.91 (3H, d, J=6.9 Hz, $H_3$-16), 0.93 (3H, d, J=6.9 Hz, $H_3$-17), 1.22 (3H, d, J=7.3 Hz, $H_3$-18), 1.78 (3H, br s, $H_3$-19), 3.89 (1H, d, J=12.4 Hz, H-20a), 3.79 (1H, d, J=12.4 Hz, H-20b), 1.87 (2H, m, $H_2$-2'), 1.54 (2H, m, $H_2$-3'), 1.27-1.30 (8H, m, H-4'-H-7'), 1.30 (2H, m, $H_2$-8'), 1.26 (2H, m, $H_2$-9'), 0.87 (3H, t, J=6.8 Hz, H-10'); 12-OAc: 2.00 (3H, s); $^{13}C$ NMR ($CDCl_3$, 100 MHz) $\delta_C$ 160.9 (C-1), 136.6 (C-2), 209.7 (C-3), 72.2 (C-4), 72.0 (C-5), 60.4 (C-6), 64.5 (C-7), 35.5 (C-8), 77.2 (C-9), 47.5 (C-10), 44.0 (C-11), 77.5 (C-12), 83.6 (C-13), 80.0 (C-14), 31.3 (C-15), 16.6 (C-16), 15.9 (C-17), 18.1 (C-18), 9.8 (C-19), 65.2 (C-20), 119.9 (C-1'), 34.8 (C-2'), 23.4 (C-3'), 29.6 (C-4'), 29.5 (C-5'), 29.5 (C-6'), 29.3 (C-7'), 22.7 (C-8'), 31.8 (C-9'), 14.1 (C-10'); 12-OAc: 169.9, 21.2; HRESIMS m/z 593.3315 $[M+H]^+$ (calcd for $C_{32}H_{49}O_{10}^+$, 593.3320).

Example 11: Preparation of Compound YH-38

Compound YH-22 (20 mg) was taken and dissolved in 3 mL of methanol. Thirty (30) mg of palladium-carbon catalyst was then added, and hydrogen was added for protection after vacuuming. Followed by stirring for reaction at 50° C. for 30 min, the palladium-carbon was removed by filtration. The filtrate was concentrated, and then purified with an HPLC ($MeCN/H_2O$, 95%, 3 mL/min), and finally Compound YH-38 (9 mg, $t_R$=15 min) was obtained. The structure and data of the compound were as follows:

YH-38

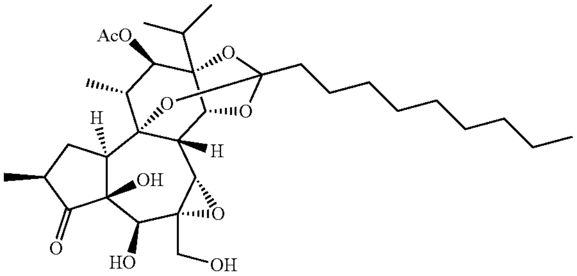

YH-38: $[\alpha]^{25}$+76.8 (c 0.67, MeOH); UV (MeOH) $\lambda_{max}$ (log) 202 (3.50) nm; IR (KBr) $v_{max}$ 3463, 2927, 1742, 1378, 1229, 1028, and 940 $cm^{-1}$; $^1H$ NMR ($CDCl_3$, 500 MHz) δ111.53 (1H, m, H-la), 2.28 (1H, m, H-1b) 2.28 (1H, m, H-2), 4.07 (1H, s, H-5), 3.44 (1H, s, H-7), 3.32 (1H, s, H-8), 2.84 (1H, m, H-10), 2.25 (1H, m, H-11), 5.03 (1H, s, H-12), 4.40 (1H, s, H-14), 1.83 (1H, m, H-15), 0.93 (3H, d, J=6.7 Hz, $H_3$-16), 0.93 (3H, d, J=6.7 Hz, $H_3$-17), 1.25 (3H, d, J=7.3 Hz, $H_3$-18), 1.10 (3H, d, J=5.5 Hz, $H_3$-19), 3.87 (1H, d, J=12.2 Hz, H-20a), 3.75 (1H, d, J=12.2 Hz, H-20b), 1.84 (2H, m, $H_2$-2'), 1.52 (2H, m, $H_2$-3'), 1.25-1.31 (8H, m, H-4'-H-7'), 1.28 (2H, m, $H_2$-8'), 1.26 (2H, m, $H_2$-9'), 0.87 (3H, t, J=6.7 Hz, H-10'); 12-OAc: 2.00 (3H, s); $^{13}C$ NMR ($CDCl_3$, 125 MHz) $\delta_C$ 33.3 (C-1), 42.8 (C-2), 220.3 (C-3), 75.0 (C-4), 71.1 (C-5), 60.7 (C-6), 64.5 (C-7), 35.5 (C-8), 77.6 (C-9), 44.0 (C-10), 43.5 (C-11), 76.8 (C-12), 83.1 (C-13), 80.3 (C-14), 31.2 (C-15), 16.5 (C-16), 15.9 (C-17), 18.3 (C-18), 12.4 (C-19), 65.4 (C-20), 120.0 (C-1'), 34.9 (C-2'), 23.3 (C-3'), 29.6 (C-4'), 29.5 (C-5'), 29.5 (C-6'), 29.3 (C-7'), 22.6 (C-8'), 31.8 (C-9'), 14.1 (C-10'); 12-OAc: 170.0, 21.2; HRESIMS m/z 617.3316 $[M+Na]^+$ (calcd for $C_{32}H_{50}O_{10}^+$, 617.3296).

Example 12: Preparation of Compound YH-39

Compound YH-11 was taken, and the product was prepared with reference to the method in Example 11. After the obtained product was purified with an HPLC ($MeCN/H_2O$, 70%, 3 mL/min), Compound YH-39 (10 mg, $t_R$=17 min) was obtained. The structure and data of the compound were as follows:

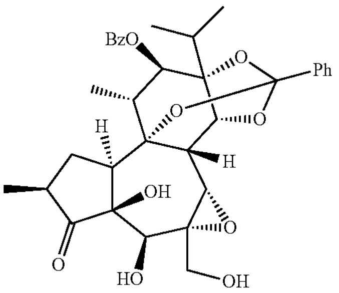

YH-39: $[\alpha]^{25}$+64.5 (c 0.067, MeOH); UV (MeOH) $\lambda_{max}$ (log) 230 (4.08) nm; IR (KBr) $v_{max}$ 3483, 2968, 1720, 1272, 1079, and 1025 $cm^{-1}$; $^1H$ NMR ($CDCl_3$, 400 MHz) δ112.36 (1H, m, H-1α), 1.61 (1H, m, H-1β), 2.25 (1H, m, H-2), 4.05 (1H, s, H-5), 3.62 (1H, s, H-7), 3.59 (1H, d, J=2.4 Hz, H-8), 3.01 (1H, dd, J=13.2, 5.8 Hz, H-10), 2.54 (1H, q, J=6.9 Hz, H-11), 5.42 (1H, s, H-12), 4.74 (1H, d, J=2.4 Hz, H-14), 2.03

(1H, m, H-15), 1.04 (3H, d, J=6.7 Hz, $H_3$-16), 1.04 (3H, d, J=6.7 Hz, $H_3$-17), 1.46 (3H, d, J=6.9 Hz, $H_3$-18), 1.09 (3H, d, J=6.6 Hz, $H_3$-19), 3.86 (1H, d, J=12.3 Hz, H-20a), 3.79 (1H, d, J=12.3 Hz, H-20b); 1'-Ph: 7.75 (2H, m), 7.39 (2H, m), 7.39 (1H, m). 12-OBz: 7.94 (2H, d, J=7.4 Hz), 7.47 (2H, dd, J=7.4, 7.4 Hz), 7.59 (1H, dd, J=7.4, 7.4 Hz); $^{13}$C NMR ($CDCl_3$, 100 MHz) $\delta_C$ 33.4 (C-1), 42.8 (C-2), 220.1 (C-3), 74.9 (C-4), 71.2 (C-5), 60.7 (C-6), 64.4 (C-7), 36.1 (C-8), 78.9 (C-9), 44.1 (C-10), 43.8 (C-11), 77.3 (C-12), 84.1 (C-13), 81.0 (C-14), 31.6 (C-15), 16.7 (C-16), 16.2 (C-17), 18.6 (C-18), 12.4 (C-19), 65.1 (C-20), 118.1 (C-1'). 1'-Ph: 135.7, 125.9×2, 128.0×2, 129.5. 12-OBz: 165.6, 129.8, 129.5×2, 128.6×2, 133.3; HRESIMS m/z 605.2407 [M−H] (calcd for $C_{34}H_{37}O_{10}^-$, 605.2392).

Example 13: Preparation of Compound YH-47 and Compound YH-48

Compound YH-6 (30 mg) was taken and dissolved in 2 mL of tetrahydrofuran (THF). Two-hundred (200) μL of concentrated hydrochloric acid was added for reaction for about 20 min under stirring, 10 mL of water was added to stop the reaction, and then EtOAc (3×10 mL) was added for extraction. After the reaction products passed through a gel (MeOH) and a preparative thin layer ($CH_2Cl_2$/MeOH, 40:1), Compound YH-47 (13 mg) and Compound YH-48 (10 mg) were obtained. The structure and data of the compounds were as follows:

YH-47

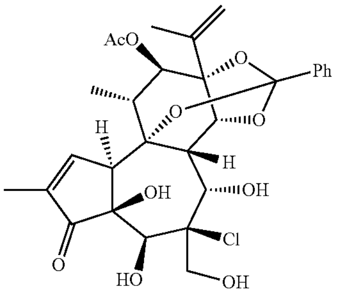

YH-48

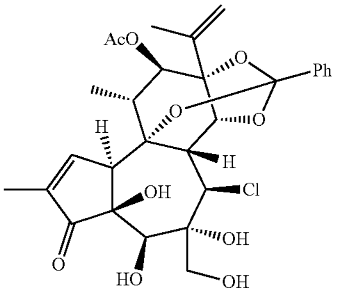

YH-47:$[\alpha]_D^{25}$+10.5 (c 0.13,MeOH); UV (MeOH) $\lambda_{max}$ (log) 241 (3.70) nm; IR (KBr) $v_{max}$ 3451, 2925, 1740, 1691, 1230, 1078, and 697 cm$^{-1}$; $^1$H NMR ($CDCl_3$, 400 MHz) $\delta_H$ 7.61 (1H, br s, H-1), 4.38 (1H, s, H-5), 4.74 (1H, s, H-7), 3.60 (1H, d, J=2.4 Hz, H-8), 4.04 (1H, m, H-10), 2.85 (1H, q, J=7.3 Hz, H-11), 5.03 (1H, s, H-12), 4.96 (1H, d, J=2.4 Hz, H-14), 5.03 (1H, s, H-16a), 5.06 (1H, s, H-16b), 1.87 (3H, s, $H_3$-17), 1.35 (3H, d, J=7.3 Hz, $H_3$-18), 1.81 (3H, br s, $H_3$-19), 4.01 (1H, d, J=11.3 Hz, H-20a), 4.16 (1H, d, J=11.3 Hz, H-20b). 1'-Ph: 7.64 (2H, m), 7.41 (2H, m), 7.40 (1H, m). 12-OAc: 1.98 (3H. s); $^{13}$C NMR ($CDCl_3$, 100 MHz) $\delta_C$ 158.6 (C-1), 136.7 (C-2), 208.6 (C-3), 75.2 (C-4), 70.9 (C-5), 76.9 (C-6), 81.4 (C-7), 36.2 (C-8), 78.9 (C-9), 49.9 (C-10), 43.5 (C-11), 77.7 (C-12), 84.7 (C-13), 82.7 (C-14), 142.4 (C-15), 113.9 (C-16), 18.7 (C-17), 17.8 (C-18), 9.9 (C-19), 68.8 (C-20), 117.7 (C-1'). 1'-Ph: 134.6, 125.8×2, 128.2×2, 130.0. 12-OAc: 169.5, 20.9; HRESIMS m/z 575.1685 [M−H](calcd. for $C_{29}H_{32}O_{10}Cl^-$, 575.1689).

YH-48:$[\alpha]_D^{25}$+15 (c 0.1, MeOH); UV (MeOH) $\lambda_{max}$ (log) 241 (3.70) nm; IR (KBr) $v_{max}$ 3451, 2925, 1740, 1691, 1230, 1078, and 697 cm$^{-1}$; $^1$H NMR ($CDCl_3$, 400 MHz) $\delta_H$ 7.59 (1H, br s, H-1), 3.96 (1H, s, H-5), 4.89 (1H, d, J=9.8 Hz, H-7), 3.06 (1H, m, H-8), 3.07 (1H, m, H-10), 2.85 (1H, q, J=7.2 Hz, H-11), 5.02 (1H, s, H-12), 5.37 (1H, d, J=2.4 Hz, H-14), 5.01 (1H, s, H-16a), 5.03 (1H, s, H-16b), 1.85 (3H, s, $H_3$-17), 1.33 (3H, d, J=7.2 Hz, $H_3$-18), 1.80 (3H, br s, $H_3$-19), 4.06 (1H, d, J=10.4 Hz, H-20a), 4.46 (1H, d, J=10.4 Hz, H-20b). 1'-Ph: 7.67 (2H, m), 7.39 (2H, m), 7.39 (1H, m). 12-OAc: 2.03 (3H. s); $^{13}$C NMR ($CDCl_3$, 100 MHz) $\delta_C$ 158.9 (C-1), 137.6 (C-2), 208.5 (C-3), 73.3 (C-4), 81.7 (C-5), 79.0 (C-6), 66.9 (C-7), 36.8 (C-8), 78.4 (C-9), 50.6 (C-10), 42.8 (C-11), 77.9 (C-12), 84.2 (C-13), 79.1 (C-14), 142.8 (C-15), 113.7 (C-16), 18.8 (C-17), 18.1 (C-18), 10.0 (C-19), 61.8 (C-20), 117.4 (C-1'). 1'-Ph: 134.8, 125.9×2, 128.1×2, 129.8. 12-OAc: 169.7, 21.0; HRESIMS m/z 575.1681 $[M-H]^-$ (calcd. for $C_{29}H_{32}O_{10}Cl^-$, 575.1689).

Example 14: Preparation of Compound YH-49 and Compound YH-50

Compound YH-11 (40 mg) was taken, and the product was prepared by using the same method in Example 13. After purifying the obtained product with a preparative thin layer ($CH_2Cl_2$/MeOH, 50:1), Compound YH-49 (20 mg) and Compound YH-50 (12 mg) were obtained. The structure and data of the compounds were as follows:

YH-49

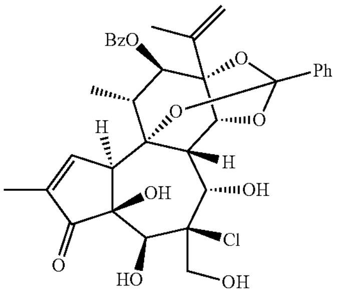

YH-50

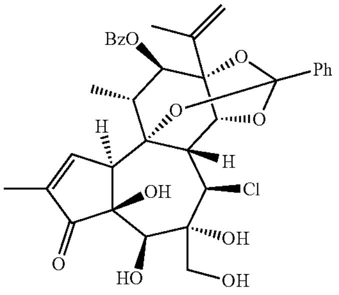

YH-49:$[\alpha]_D^{25}$+23.6 (c 0.46,MeOH); UV (MeOH) $\lambda_{max}$ (log) 231 (4.01) nm; IR (KBr) $v_{max}$ 3450, 2924, 1721, 1268, 1079, and 711 cm$^{-1}$; $^1$H NMR ($CDCl_3$, 400 MHz) $\delta_H$ 7.64 (1H, s, H-1), 4.40 (1H, s, H-5), 4.84 (1H, s, H-7), 3.79 (1H, d, J=2.4 Hz, H-8), 4.08 (1H, m, H-10), 2.99 (1H, q, J=7.3 Hz, H-11), 5.34 (1H, s, H-12), 5.10 (1H, d, J=2.4 Hz, H-14), 5.07 (1H, s, H-16a), 5.03 (1H, s, H-16b), 1.91 (3H, s, $H_3$-17), 1.45 (3H, d, J=7.3 Hz, $H_3$-18), 1.81 (3H, br s, $H_3$-19), 4.16 (1H, d, J=11.5 Hz, H-20a), 4.02 (1H, d, J=11.5 Hz, H-20b). 1'-Ph: 7.68 (2H, m), 7.42 (2H, m), 7.44 (1H, m). 12-OBz: 7.97 (2H, m), 7.42 (2H, m), 7.55 (1H, t, J=7.4 Hz); $^{13}$C NMR ($CDCl_3$, 100 MHz) $\delta_C$ 158.6 (C-1), 136.9 (C-2), 208.6 (C-3), 75.1 (C-4), 70.9 (C-5), 77.0 (C-6), 81.6 (C-7), 36.6 (C-8), 79.1 (C-9), 49.9 (C-10), 43.8 (C-11), 78.0 (C-12), 85.1 (C-13), 82.9 (C-14), 142.4 (C-15), 114.2 (C-16), 18.8 (C-17), 18.0 (C-18), 9.9 (C-19), 68.9 (C-20), 117.9 (C-1'). 1'-Ph: 134.6, 125.8×2, 128.3×2, 130.1. 12-OBz: 165.1, 129.4, 129.6×2, 128.4×2, 133.4; HRESIMS m/z 637.18513 $[M-H]^-$ (calcd for $C_{34}H_{34}O_{10}Cl^-$, 637.18460).

YH-50: $[\alpha]_D^{25}$+16.7 (c 0.35, MeOH); UV (MeOH) $\lambda_{max}$ (log) 230 (4.10) nm; IR (KBr) $v_{max}$ 3431, 2960, 1721, 1451, 1268, and 1075 $cm^{-1}$; $^1$H NMR ($CDCl_3$, 500 MHz) $\delta_H$ 7.62 (1H, br s, H-1), 3.90 (1H, s, H-5), 4.90 (1H, d, J=9.9 Hz, H-7), 3.12 (1H, d, J=9.9 Hz, H-8), 3.06 (1H, br s, H-10), 2.99 (1H, q, J=7.2 Hz, H-11), 5.28 (1H, s, H-12), 5.51 (1H, s, H-14), 5.06 (1H, s, H-16a), 5.01 (1H, s, H-16b), 1.88 (3H, s, $H_3$-17), 1.44 (3H, d, J=7.2 Hz, H-18), 1.78 (3H, br s, H-19), 4.33 (1H, d, J=11.1 Hz, H-20a), 4.06 (1H, d, J=11.1 Hz, H-20b). 1'-Ph: 7.71 (2H, d, J=7.3 Hz), 7.42 (2H, m), 7.43 (1H, m). 12-OBz: 7.94 (2H, d, 7.4), 7.47 (2H, m), 7.59 (1H, t, J=7.4 Hz); $^{13}$C NMR ($CDCl_3$, 125 MHz) $\delta_C$ 158.9 (C-1), 137.6 (C-2), 208.4 (C-3), 73.1 (C-4), 81.8 (C-5), 78.5 (C-6), 66.5 (C-7), 37.1 (C-8), 78.4 (C-9), 50.4 (C-10), 43.0 (C-11), 78.5 (C-12), 84.4 (C-13), 79.2 (C-14), 142.8 (C-15), 114.0 (C-16), 18.9 (C-17), 18.3 (C-18), 10.0 (C-19), 62.1 (C-20), 117.5 (C-1'). 1'-Ph: 134.8, 125.9×2, 128.2×2, 130.1. 12-OBz: 165.0, 129.4, 129.4×2, 128.7×2, 133.6; HRESIMS m/z 637.18536 $[M-H]^-$ (calcd for $C_{34}H_{34}O_{10}Cl^-$, 637.18460).

Example 15: Preparation of Compound YH-52 and Compound YH-53

Compound YH-11 (100 mg) was taken and dissolved in 3 mL of dichloromethane, then stirred at −60° C. for 5 minutes, and $PBr_3$ (50 μL) was added. After the thin layer detects the end of the reaction, the reaction solution was taken out and then quenched by the addition of 5 mL of water. Followed by adding dichloromethane for extraction (3×5 mL), the organic layer was combined, concentrated under a reduced pressure, then purified with a semi-preparative high-performance liquid phase (MeCN/$H_2O$, 80: 20, 3 mL/min), and finally Compound YH-52 (23 mg, $t_R$=15 min) and Compound YH-53 (20 mg, $t_R$=12 min) were obtained. The structure and data of the compounds were as follows:

YH-52

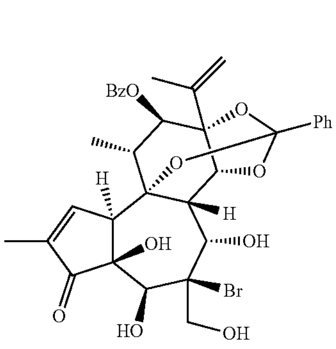

-continued

YH-53

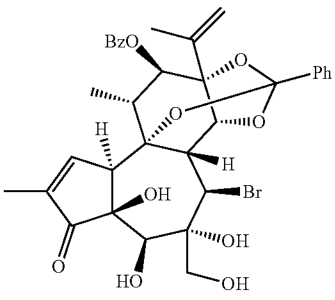

YH-52: $[\alpha]_D^{25}$+56.3 (c 0.35, MeOH); UV (MeOH) $\lambda_{max}$ (log) 232 (3.96) nm; IR (KBr) $v_{max}$ 3445, 2923, 1720, 1692, 1268, 1078, 1008, and 710 $cm^{-1}$; $^1$H NMR ($CDCl_3$, 400 MHz) $\delta_H$ 7.64 (1H, s, H-1), 4.27 (1H, s, H-5), 4.98 (1H, s, H-7), 3.88 (1H, d, J=2.4 Hz, H-8), 4.08 (1H, s, H-10), 3.00 (1H, q, J=7.3 Hz, H-11), 5.33 (1H, s, H-12), 5.11 (1H, d, J=2.4 Hz, H-14), 5.04 (1H, s, H-16a), 5.08 (1H, s, H-16b), 1.91 (3H, s, $H_3$-17), 1.45 (3H, d, J=7.3 Hz, $H_3$-18), 1.81 (3H, br s, $H_3$-19), 4.10 (1H, d, J=12.0 Hz, H-20a), 4.21 (1H, m, H-20b), 12-OBz: 8.01 (2H, m), 7.39 (2H, m), 7.55 (1H, m); 1'-Ph: 7.68 (2H, m), 7.44 (3H, m); $^{13}$C NMR ($CDCl_3$, 100 MHz) $\delta_C$ 158.6 (C-1), 136.9 (C-2), 208.7 (C-3), 75.1 (C-4), 70.5 (C-5), 75.8 (C-6), 82.5 (C-7), 37.8 (C-8), 79.2 (C-9), 50.0 (C-10), 43.8 (C-11), 78.1 (C-12), 85.1 (C-13), 82.8 (C-14), 142.4 (C-15), 114.2 (C-16), 18.8 (C-17), 18.0 (C-18), 9.9 (C-19), 69.9 (C-20), 117.9 (C-1'), 1'-Ph: 134.5, 125.8×2, 128.4×2, 130.1, 12-OBz: 165.1, 129.3, 129.8×2, 128.3×2, 133.4; HRESIMS m/z 705.1309 $[M+Na]^+$ (calcd for, $C_{34}H_{35}O_{10}BrNa^+$, 705.1306).

YH-53: $[\alpha]^{25}$+50.0 (c 0.30, MeOH); UV (MeOH) $\lambda_{max}$ (log) 232 (4.06) nm; IR (KBr) $v_{max}$ 3428, 1701, 1452, 1268, 1079, 1026, and 712 $cm^{-1}$; $^1$H NMR ($CDCl_3$, 500 MHz) $\delta_H$ 7.57 (1H, s, H-1), 3.85 (1H, s, H-5), 5.06 (1H, d, J=9.9 Hz, H-7), 3.12 (1H, d, J=9.9 Hz, H-8), 3.07 (1H, br s, H-10), 3.00 (1H, q, J=7.2 Hz, H-11), 5.28 (1H, s, H-12), 5.57 (1H, d, J=1.3 Hz, H-14), 5.00 (1H, s, H-16a), 5.04 (1H, s, H-16b), 1.88 (3H, s, $H_3$-17), 1.42 (3H, d, J=7.2 Hz, $H_3$-18), 1.73 (3H, br s, $H_3$-19), 4.09 (1H, d, J=10.9 Hz, H-20a), 4.39 (1H, d, J=10.9 Hz, H-20b), 12-OBz: 7.93 (2H, d, J=7.5 Hz), 7.46 (2H, dd, J=7.5, 7.5 Hz), 7.56 (1H, m); 1'-Ph: 7.71 (2H, m), 7.42 (2H, m), 7.41 (1H, m); $^{13}$C NMR ($CDCl_3$, 125 MHz) $\delta_C$ 158.8 (C-1), 137.5 (C-2), 208.2 (C-3), 73.4 (C-4), 81.1 (C-5), 78.2 (C-6), 63.7 (C-7), 36.9 (C-8), 78.5 (C-9), 50.7 (C-10), 43.0 (C-11), 78.4 (C-12), 84.7 (C-13), 81.8 (C-14), 142.7 (C-15), 114.0 (C-16), 18.9 (C-17), 18.2 (C-18), 9.9 (C-19), 63.6 (C-20), 117.3 (C-1'), 1'-Ph: 134.9, 125.9×2, 128.1×2, 129.8, 12-OBz: 165.0, 129.4, 129.4×2, 128.7×2, 133.6; HRESIMS m/z 705.1289 $[M+Na]^+$ (calcd for, $C_{34}H_{35}O_{10}BrNa^+$, 705.1306).

Inhibitory Activity of Daphnane Diterpenoid Compound on Castration-Resistant Prostate Cancer Cells (1) Cells Culture All prostate cancer cells were cultured with a RPMI-1640 medium containing 10% calf serum, 100 units of penicillin per milliliter and 100 g/mL of streptomycin in a constant temperature incubator containing 5% carbon dioxide at a saturated humidity of 37° C.

(2) Cytotoxic Activity Test

Cells in the logarithmic phase of growth were taken and cultured in 96-well plates for 24 hours ($5\times10^3$ cells/well), then treated with different concentrations of the compounds to be tested, and incubated by MTT method for 4 hours. The supernatant was removed by centrifugation, the MTT crystals were dissolved by adding DMSO, and the absorbance value was measured by an enzyme-linked immunosorbent assay at a wavelength of 570 nm. The cytotoxic activity of the compounds to be tested on cancer cells was expressed as $IC_{50}$.

YH-12, YH-19, YH-20, YH-25, etc. Additionally, the 6,7-epoxy had a significantly reduced activity when being ring-opened to form a dihydroxy product YH-51, and had an enhanced activity and a significantly reduced toxicity for the normal human prostate cell RWPE-1 than that of prototype compound YH-11 when being ring-opened to form a bromination product YH-52. Such compounds having modifications to the 1'-olefin side chain had unforeseen effects on activity, but overall, compounds with 1'-olefin side chains were more cytotoxic, for example, the compounds YH-16 and YH-22 were more cytotoxic than compounds YH-11 and YH-6. Compounds YH-52 was selected as a candidate for in vivo pharmacodynamic evaluation in animals.

TABLE 1 inhibitory activity of representative daphnane diterpenoids compounds on several human prostate cancer cells and normal cells

| | Prostate cancer cells $IC_{50}$ (μM) | | | | | Normal cells |
|---|---|---|---|---|---|---|
| No. | C4-2B | C4-2B/ENZR | LNcap | Vcap-CRPC | 22RV1 | RWPE-1 |
| YH-1 | $3.41 \times e^{-6}$ | $1.56 \times e^{-4}$ | $3.76 \times e^{-5}$ | $1.41 \times e^{-5}$ | 0.00574 | 43.5 |
| YH-2 | $8.21 \times e^{-5}$ | $3.36 \times e^{-5}$ | $4.25 \times e^{-5}$ | $1.17 \times e^{-5}$ | 0.0265 | 40.3 |
| YH-3 | 0.00895 | $4.03 \times e^{-4}$ | 0.00377 | 0.00174 | 0.434 | 57.2 |
| YH-5 | 0.904 | 0.434 | 0.0993 | 4.66 | 44.5 | 72.8 |
| YH-6 | 0.000367 | 0.00234 | 0.00389 | 0.0212 | 0.0525 | 44.2 |
| YH-9 | 0.380 | 1.462 | NA | NA | NA | NA |
| YH-11 | $8.14 \times e^{-7}$ | $2.46 \times e^{-7}$ | $3.31 \times e^{-7}$ | $2.93 \times e^{-7}$ | $1.36 \times e^{-4}$ | 13.4 |
| YH-12 | 0.557 | 1.90 | NA | NA | NA | NA |
| YH-13 | $7.10 \times e^{-3}$ | 0.00679 | 0.00453 | 0.0672 | 0.0832 | 35.7 |
| YH-16 | $3.42 \times e^{-4}$ | $2.32 \times e^{-4}$ | 0.00543 | 0.00570 | 0.0332 | 9.67 |
| YH-19 | 0.0644 | 0.136 | NA | NA | NA | NA |
| YH-20 | 1.578 | 5.76 | NA | NA | NA | NA |
| YH-22 | $1.62 \times e^{-8}$ | $1.66 \times e^{-7}$ | $2.31 \times e^{-6}$ | $5.63 \times e^{-7}$ | $3.46 \times e^{-4}$ | 5.89 |
| YH-24 | $1.97 \times e^{-3}$ | 0.0673 | 0.0482 | 0.0762 | 0.0458 | 21.9 |
| YH-25 | 0.593 | 2.30 | NA | NA | NA | NA |
| YH-30 | 0.0219 | 0.0368 | 0.00248 | 0.171 | 7.23 | 73.5 |
| YH-35 | 0.000426 | 0.00192 | 0.00482 | 0.0642 | 0.144 | 42.9 |
| YH-36 | $3.15 \times e^{-4}$ | $8.46 \times e^{-5}$ | $3.96 \times e^{-4}$ | $1.53 \times e^{-6}$ | 0.0425 | 14.6 |
| YH-37 | $9.98 \times e^{-8}$ | $1.45 \times e^{-7}$ | $2.22\ e^{-5}$ | $1.26 \times e^{-4}$ | $5.08 \times e^{-4}$ | 10.3 |
| YH-38 | $1.56 \times e^{-6}$ | $1.23 \times e^{-5}$ | $2.76 \times e^{-4}$ | $9.02 \times e^{-4}$ | 0.00542 | 20.6 |
| YH-39 | $2.99 \times e^{-5}$ | $2.32 \times e^{-5}$ | $2.98 \times e^{-4}$ | $7.90 \times e^{-4}$ | 0.00673 | 18.5 |
| YH-40 | $3.59 \times e^{-6}$ | $9.34 \times e^{-5}$ | $3.02 \times e^{-5}$ | $2.20 \times e^{-4}$ | $1.20 \times e^{-4}$ | 20.3 |
| YH-44 | 0.193 | 0.641 | 0.0748 | 0.306 | 4.65 | 17.4 |
| YH-51 | 0.00781 | 0.0774 | 0.00251 | 0.00202 | 1.77 | 12.3 |
| YH-52 | $5.17 \times e^{-7}$ | $4.66 \times e^{-8}$ | $4.22 \times e^{-6}$ | $5.93 \times e^{-8}$ | $9.67 \times e^{-5}$ | 53.6 |
| YH-53 | $2.35 \times e^{-6}$ | $5.77 \times e^{-5}$ | $3.56 \times e^{-5}$ | $4.33 \times e^{-4}$ | $1.98 \times e^{-4}$ | 56.3 |
| YH-56 | 4.47 | 2.69 | 13.1 | 15.4 | 47.1 | 35.1 |
| YH-57 | 2.32 | 1.87 | 4.82 | 40.8 | 46.7 | 41.1 |
| YH-58 | 33.6 | 40.2 | NA | NA | NA | NA |
| YH-60 | 0.0494 | 0.0739 | 0.00285 | 0.911 | 3.89 | 4.81 |
| YH-61 | 0.189 | 0.543 | NA | NA | NA | NA |
| ENZ | 24.8 | 62.3 | 20.7 | 57.3 | 39.4 | NA |
| DOX | 0.00104 | 0.00287 | $2.55 \times e^{-5}$ | 0.0124 | 0.00599 | 0.0333 |

ENZ: a positive drug enzalutamide; DOX: a positive drug doxorubicin; and NA means not tested for a low activity.

(3) Experimental Results

As shown in Table 1, most of the daphnane diterpenoids showed different degrees of activity in inhibiting a variety of prostate cancer cells. Some representative compounds had a significant inhibitory activity on prostate cancer cells, with an $IC_{50}$ at an nM level, which were stronger than that of the positive drugs doxorubicin and enzalutamide (ENZ), among which the activity of the compounds YH-11, YH-22 and YH-52 were the most prominent. A preliminary structure-activity relationship analysis showed that the inhibitory activity of the compounds that contain 9,13,14-orthoesters (YH-11 and YH-52, etc.) was significantly higher than that of compounds without orthoesters (YH-56, YH-60 and YH-61), which indicated that the orthoester was the key pharmacophore. Next, the substitution of 20-OH by an ester-philic groups may lead to a significant decrease in activity, such as the activity of the compounds YH-5, YH-9, In Vivo Pharmacodynamic Evaluation of Compound YH-52 in Animals (1) Construction of a Mice Model for 22RV1 Prostate Cancer Growth First, a large number of 22RV1 cells were amplified. To ensure the success rate of tumor-bearing, the cell state needs to be adjusted to the optimal state. When the number of the cells was sufficient, the cells were digested and flushed twice with PBS buffer to remove fetal bovine serum (FBS) from the medium to reduce immune rejection. The cells were adjusted to $3000*10^4$/mL after counting by a hemocytometer. Then 22Rv1 human prostate cancer cells (1004) were subcutaneously injected into a 4-5 weeks old nod-scid male mice with severe immunodeficiency.

(2) Grouping and Administration

Figure 2A:
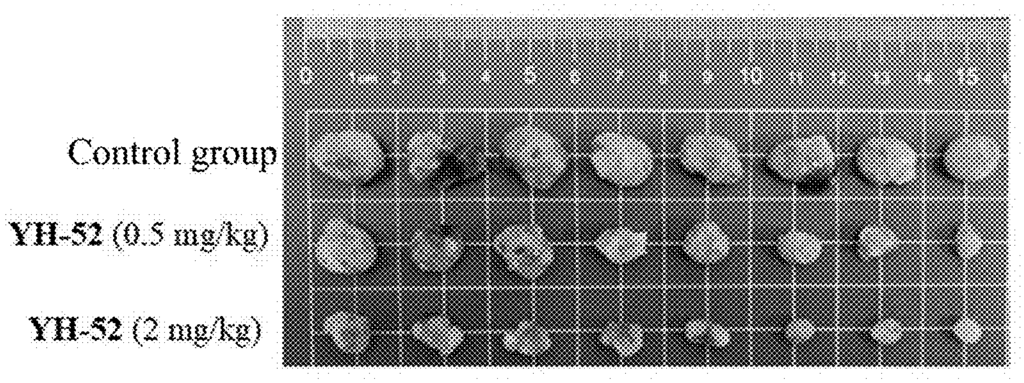
FIG. 2A shows the effect of oral administration of Compound YH-52 on the size of tumor.
Figure 2B:
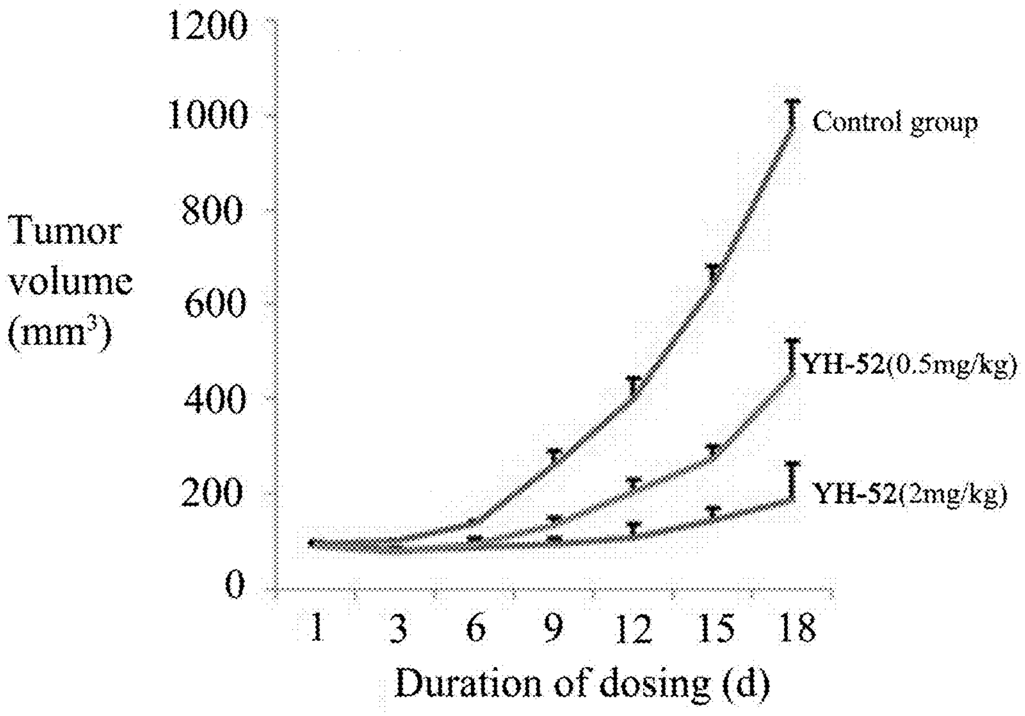
FIG. 2B shows the effect of oral administration of Compound YH-52 on the volume of tumor.
Figure 2C:
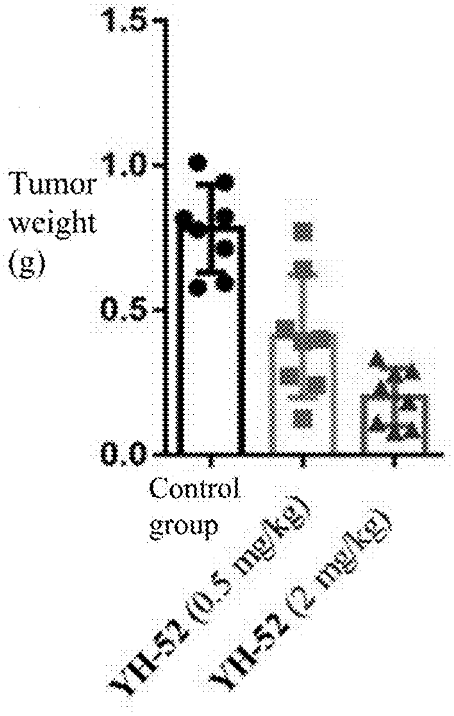
FIG. 2C shows the effect of oral administration of Compound YH-52 on the weight of tumor.
Figure 3A:
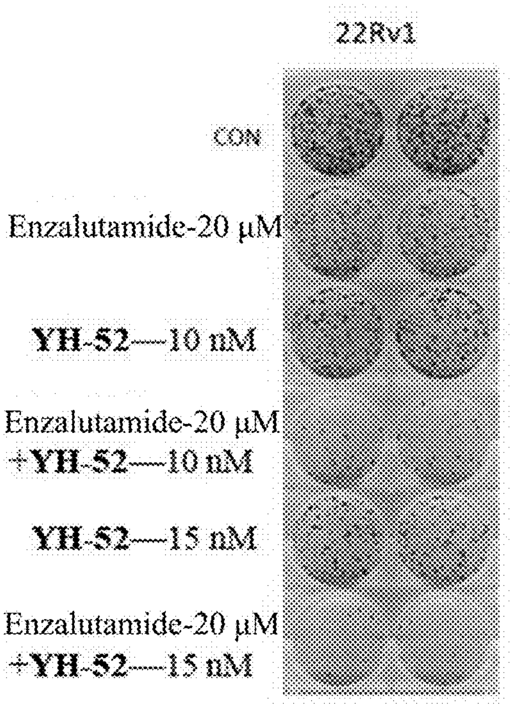
FIG. 3A shows the inhibitory effect of intraperitoneal injection administration of Compound YH-52 combined with enzalutamide on prostate cancer cells 22RV1.
Figure 3B:
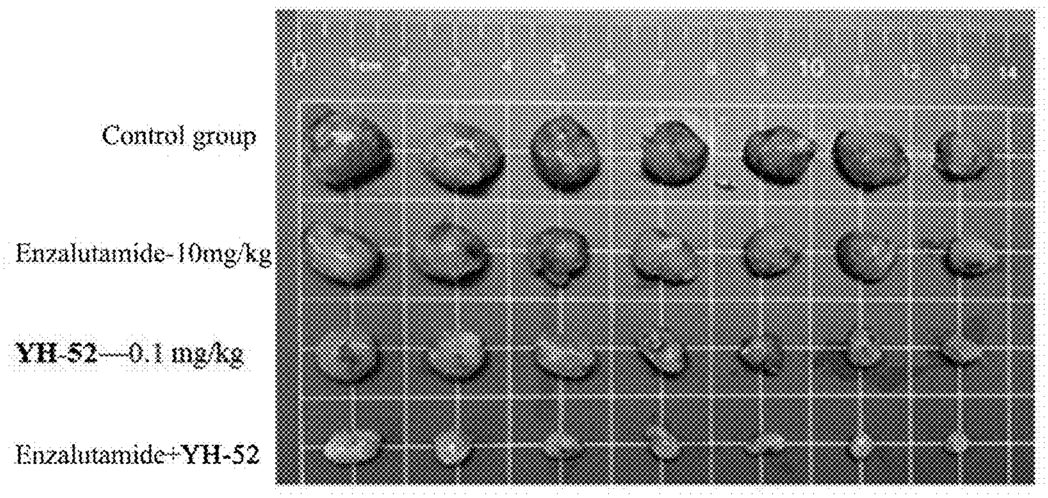
FIG. 3B shows the effect of intraperitoneal injection administration of Compound YH-52 combined with enzalutamide on the size of tumor.
Figure 3C:
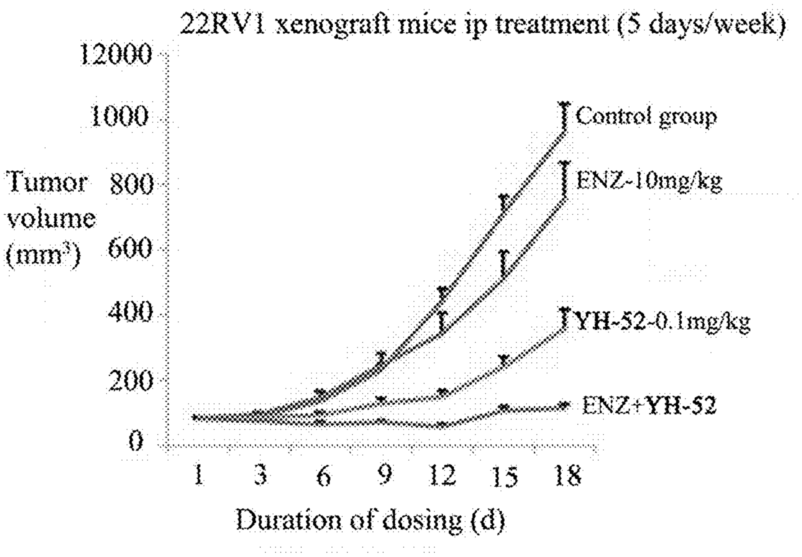
FIG. 3C shows the effect of intraperitoneal injection administration of Compound YH-52 combined with enzalutamide on the volume of tumor.
Figure 3D:
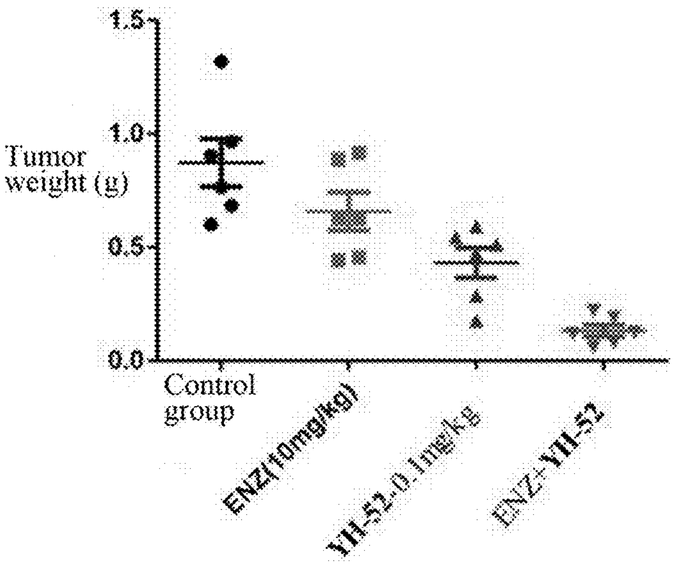
FIG. 3D shows the effect of intraperitoneal injection administration of Compound YH-52 combined with enzalutamide on the weight of tumor.

Oral Administration Experiment:

When the tumor grew to a volume of about 100 $mm^3$, the mice were randomly divided into 3 groups to make sure that the average tumor volume was the same. The mice in the dosing group were orally gavaged with 0.5 mg/kg and 2 mg/kg of Compound YH-52 per day, and the mice in the control group were given the same volume of normal saline containing DMSO. The body weight of the mice and the length and width of the tumors were measured and recorded every 3 days. The subcutaneous tumors were taken and then photographed at the end of the experiment. The tumor volumes were calculated according to the equation: volume=length×width$^2$×π/6, and then counted. The experimental results are shown in FIG. 2A, FIG. 2B and FIG. 2C.

Experiment of Intraperitoneal Injection Administration in Combination with Enzalutamide:

When the tumor grew to about 100 $mm^3$, the mice were randomly divided into 4 groups to make sure that the average tumor volume was the same. The mice in the dosing group were intraperitoneally injected with 0.1 mg/kg of Compound YH-52 per day, the mice in the positive drug group were intraperitoneally injected with 10 mg/kg of enzalutamide per day, the mice in the combination group were intraperitoneally injected with 0.1 mg/kg of Compound YH-52 and 10 mg/kg of enzalutamide per day, and the mice in the control group were given the same volume of normal saline containing DMSO. The body weight of the mice and the length and width of the tumor were measured and recorded every 3 days. The subcutaneous tumors were taken and then photographed at the end of the experiment. The tumor volumes were calculated according to the equation: volume=length×width$^2$×π/6, and then counted. The experimental results are shown in FIG. 3A, FIG. 3B, FIG. 3C and FIG. 3D.

(3) Experimental Results

As shown in FIG. 2A, FIG. 2B and FIG. 2C, Compound YH-52 could significantly inhibit tumor growth in mice at an oral gavage dose of 0.5 mg/kg and 2 mg/kg. As shown in FIG. 3A, FIG. 3B, FIG. 3C and FIG. 3D, compared to the positive drug enzalutamide (ENZ), Compound YH-52 administrated by intraperitoneal injection (at a dose of 0.1 mg/kg) showed a greater efficacy, and has a significant synergistic effect at a dose of 0.1 mg/kg when being administrated by intraperitoneal injection in combination with ENZ (10 mg/kg).

It is foreseeable that pharmaceutically acceptable salts of the compound can produce the same or similar activity.

The invention claimed is:

1. A method for treatment or adjuvant treatment of a castration-resistant prostate cancer in a patient, comprising:

determining whether the patient suffers from the castration-resistant prostate cancer, and administering to the patient a therapeutic amount of a daphnane diterpenoid compound of formula I or a pharmaceutically acceptable salt thereof;

I

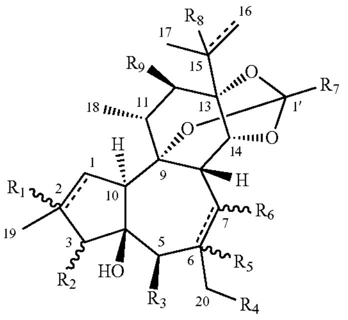

wherein:

in the formula I, a bond between C-1 and C-2 is a double bond, a bond between C-6 and C-7 is a single bond, and a bond between C-15 and C-16 is a double bond;

$R_1$ is absent;

$R_2$ is carbonyl;

$R_3$ is hydroxyl;

$R_4$ is hydroxyl;

$R_5$ is fluorine, chlorine, bromine, or iodine;

$R_6$ is fluorine, chlorine, bromine, or iodine;

$R_7$ is phenyl;

$R_8$ is absent; and $R_9$ is hydrogen, hydroxyl, acetyl, benzoyl, isobutyryl, butyryl, or propionyl.

2. The method according to claim 1, further comprising administering to the patient at least one compound having a therapeutic effect on the castration-resistant prostate cancer.

3. The method according to claim 2, wherein the compound having the therapeutic effect on the castration-resistant prostate cancer is selected from the group consisting of enzalutamide, abiraterone, cyclophosphamide, adriamycin, docetaxel, mitoxantrone, and combinations thereof.

4. A method for treatment or adjuvant treatment of a castration-resistant prostate cancer in a patient, comprising determining whether the patient suffers from the castration-resistant prostate cancer, and administering to the patient a therapeutic amount of a daphnane diterpenoid compound of formula IV or a pharmaceutically acceptable salt thereof;

(IV)

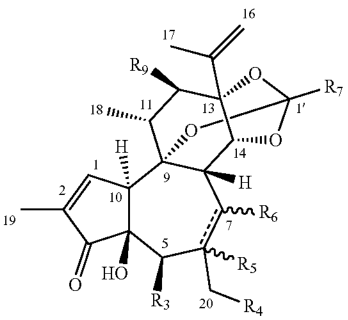

wherein the compound of formula IV is selected from the group consisting of.

| Compound | $R_3$ | $R_4$ | $R_5$ | $R_6$ | $R_7$ | $R_9$ |
|---|---|---|---|---|---|---|
| YH-45 | OH | OBz | βCl | αOH | Ph | OAc |
| YH-46 | OH | OBz | αOH | βCl | Ph | OAc |
| YH-47 | OH | OH | βCl | αOH | Ph | OAc |
| YH-48 | OH | OH | αOH | βCl | Ph | OAc |
| YH-49 | OH | OH | βCl | αOH | Ph | OBz |
| YH-50 | OH | OH | αOH | βCl | Ph | OBz |
| YH-52 | OH | OH | βBr | αOH | Ph | OBz |
| YH-53 | OH | OH | αOH | βBr | Ph | OBz |

5. The method according to claim 4, further comprising administering to the patient at least one compound having a therapeutic effect on the castration-resistant prostate cancer.

6. The method according to claim 4, wherein the compound having the therapeutic effect on the castration-resistant prostate cancer is selected from the group consisting of enzalutamide, abiraterone, cyclophosphamide, adriamycin, docetaxel, mitoxantrone, and combinations thereof.

* * * * *